US010273287B2

(12) United States Patent
Phopase

(10) Patent No.: US 10,273,287 B2
(45) Date of Patent: Apr. 30, 2019

(54) COLLAGEN MIMETIC PEPTIDE

(71) Applicant: UAB FERENTIS, Vilnius (LT)

(72) Inventor: Jaywant Babasaheb Phopase, Linköping (SE)

(73) Assignee: UAB FERENTIS, Vilnius (LT)

(*) Notice: Subject to any disclaimer, the term of this patent is extended or adjusted under 35 U.S.C. 154(b) by 0 days.

(21) Appl. No.: 15/566,034

(22) PCT Filed: Oct. 6, 2015

(86) PCT No.: PCT/EP2015/073010
§ 371 (c)(1),
(2) Date: Oct. 12, 2017

(87) PCT Pub. No.: WO2016/165788
PCT Pub. Date: Oct. 20, 2016

(65) Prior Publication Data
US 2018/0111979 A1 Apr. 26, 2018

(30) Foreign Application Priority Data

Apr. 14, 2015 (GB) .................................. 1506316.7
Apr. 15, 2015 (GB) .................................. 1506360.5

(51) Int. Cl.
A61K 38/00 (2006.01)
C07K 14/78 (2006.01)
A61L 27/22 (2006.01)
A61L 27/38 (2006.01)
A61L 27/50 (2006.01)
A61L 27/52 (2006.01)
A61L 27/54 (2006.01)
A61L 27/24 (2006.01)
A61F 2/14 (2006.01)

(52) U.S. Cl.
CPC .............. C07K 14/78 (2013.01); A61L 27/22 (2013.01); A61L 27/24 (2013.01); A61L 27/3813 (2013.01); A61L 27/3834 (2013.01); A61L 27/50 (2013.01); A61L 27/52 (2013.01); A61L 27/54 (2013.01); A61F 2/142 (2013.01); A61L 2430/16 (2013.01)

(58) Field of Classification Search
None
See application file for complete search history.

(56) References Cited

U.S. PATENT DOCUMENTS

2014/0142200 A1 5/2014 Duan et al.

FOREIGN PATENT DOCUMENTS

| WO | WO 2006042272 A2 | 4/2006 |
| WO | WO 2007069666 A1 | 6/2007 |
| WO | WO-2013023137 A2 | 2/2013 |
| WO | WO-2013078091 A1 | 5/2013 |
| WO | WO-2015032985 A1 | 3/2015 |
| WO | WO-2015055656 A1 | 4/2015 |

OTHER PUBLICATIONS

International Search Report and Written Opinion dated Jan. 20, 2016 for PCT Application No. PCT/EP2015/073010.
Islam, et al., "Functional fabrication of recombinant human collagen—phosphorylcholine hydrogels for regenerative medicine applications", Acta Biomaterialia Inc., 2015, pp. 70-80.
Deng, et al., "Collagen and glycopolymer based hydrogel for potential corneal application", Acta Biomaterialia Inc., 2010, pp. 187-194.
Liu, et al., "A Simple, Cross-linked Collagen Tissue Substitute for Corneal Implantation", Investigative Ophthalmology & Visual Science, May 2006, vol. 47, No. 5, pp. 1869-1875.
Vora, et al., "Management of Glaucoma Following Boston Keratoprosthesis", Massachusetts Eye and Ear Infirmary, Department of Ophthalmology, Harvard Medical School, Boston, Massachusetts, US, Touch Medical Media, 2012, European Ophthalmic Review, pp. 214-217.

Primary Examiner — Jeanette M Lieb
(74) Attorney, Agent, or Firm — Moser Taboada

(57) ABSTRACT

This disclosure relates to a novel Collagen Mimetic Peptide; a multi-arm conjugate comprising said peptide that mimics the higher order triple helical self-assembly of a collagen; a hydrogel comprising said Collagen Mimetic Peptide, optionally comprising collagen and optionally comprising a chemically modified surface; a corneal implant based on said hydrogel/modified hydrogel comprising a transparent central portion formed by an interpenetrating network comprising one or more additional biocompatible polymers wherein the central portion is adapted to remain cell free to ensure unhindered transmission of light.

Figure 1:
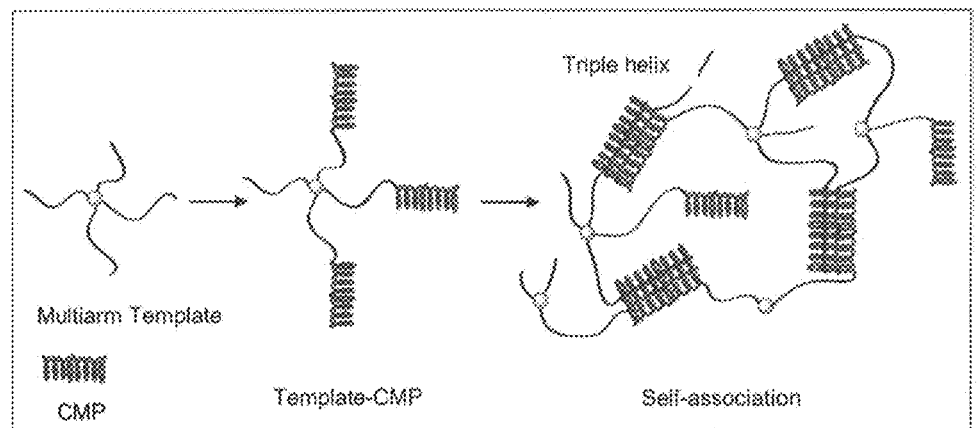

20 Claims, 22 Drawing Sheets
Specification includes a Sequence Listing.

Before UV Exposure    After UV Exposure

COLLAGEN MIMETIC PEPTIDE

FIELD OF THE INVENTION

This disclosure relates to a novel Collagen Mimetic Peptide; a multi-arm conjugate comprising said peptide that mimics the higher order triple helical self-assembly of a collagen; a hydrogel comprising said Collagen Mimetic Peptide, optionally comprising collagen and optionally comprising a chemically modified and/or patterned surface; a corneal implant based on said hydrogel/modified hydrogel comprising a transparent central portion formed by an interpenetrating network comprising one or more additional biocompatible polymers wherein the central portion is adapted to remain cell free to ensure unhindered transmission of light.

Advantageously, the implant is tolerated by the immune system, has minimal side effects and when applied to a damaged or diseased eye regenerates corneal tissue.

BACKGROUND OF THE INVENTION

The ability to see is dependent on the actions of several structures in and around the eye. When one focuses on an object, light rays are reflected from the object to the cornea. The light rays are then bent, refracted and focused by the cornea into the eyeball, through the lens and finally to the retina. The cornea is the main refractive element in the eye and is responsible for 75-80% of the focussing of light onto the retina. The retina then converts light into electrical impulses which are transmitted through the optic nerve to the brain where the image is perceived. The cornea is a highly organised structure being composed of 3 cellular layers—an external multilayered epithelium, middle stroma, and inner corneal endothelium. The acellular largely collagenous Bowman's membrane underlies the epithelium and is often considered the anterior most portion of the stroma. Between the stroma and endothelium, lies a thinner acellular layer, the Descemet's membrane.

There are a large number of diseases and conditions that affect the function of the cornea requiring transplantation of corneal tissue from donors. Diseases such as Fuchs' dystrophy, iridocorneal endothelial syndrome, keratoconus, lattice dystrophy, ocular herpes infections, trachoma are examples. In addition physical damage to the eye, for example chemical burns, sports injuries, and shrapnel injuries during military conflict are common due to the vulnerable nature of the eye.

Existing available surgical treatments include penetrating keratoplasty (full-thickness transplantation), anterior lamellar keratoplasty (and deep lamellar keratoplasty, which removes the epithelium and damaged stroma and spares the deepest parts of the stroma and endothelium) and endothelial keratoplasty (by which the patient's endothelium is replaced with a transplanted disc of posterior stroma/Descemet's membrane/corneal endothelium or Descemet's membrane/corneal endothelium). Although corneal transplantations are increasingly successful, there is a worldwide shortage of donor organs and current supplies cannot meet the demand. Moreover, patients with severe pathologies such as chemical burns, severe infections, autoimmune conditions, have a high risk of rejecting transplanted human donor corneas. Even allografting of a single epithelial layer from stem cells bears a lifelong risk of rejection necessitating the recipient to take expensive immune-suppressant drugs with often severe adverse side effects.

The extreme shortage of donor corneas, the high risk of rejection and infection after transplantation has led to a long felt need to design materials with cornea-like characteristics which are suitable for use as prosthetics or for implantation. Materials suitable as implants must be transparent (allowing more than 85% of light transmission), of good mechanical strength to allow handling, stable against enzymatic digestion, allow cell adhesion and migration to support regeneration. Examples of attempts to design corneal implants and prosthesis are known in the prior art.

For example, WO2006042272 discloses materials suitable to artificially replace or augment a damaged or diseased cornea comprising a hydrogel based on biocompatible polymers allowing diffusion of nutrients and improved mechanical strength. The artificial cornea also comprises molecules such as proteins and peptides, for example collagen, which are covalently linked to the surface of the hydrogel to promote epithelial cell adhesion and proliferation on the non-adhesive hydrogel surface. EP2535041 discloses an interpenetrating polymeric network of two or more polymer networks creating a hydrogel matrix wherein at least one polymer is a biopolymer such as collagen. This hydrogel is biocompatible, non-toxic and suitable for use as a scaffold for tissue regeneration. Liu et al (2009) discloses collagen phosphorylcholine interpenetrating network hydrogels as corneal substitutes. Artificial corneas, transplanted into minipigs, were shown to promote re-epithelialization and nerve regeneration. Others such as US2008/0287342 have developed corneal shields consisting of a network comprising collagen-mimetic peptide-PEG polymer conjugates to deliver drugs and to provide a protective environment that promotes the healing or surgical and traumatic wounds.

Although artificial corneas based on collagen are cell friendly and allow adhesion and cell proliferation they may not be suitable as a permanent implant in all patients, particularly those with very severe pathologies (e.g. chemical burns, dry eye, infections, autoimmune disease), where there is abnormal cell growth and vascularisation can reduce transparency, which can also grow into the artificial cornea when grafted into such eyes. The cornea is an avascular structure and several attempts to mimic the natural corneal characteristics through "skirt and core" matrices aimed to provide both a translucent core and an outer skirt which enables vascularisation and cell migration. For example, US2011/0125260 discloses an artificial cornea comprising a ridged translucent core and a skirt comprising a porous hydrogel, wherein the core is made by forming a hydrogel skirt around a mould wherein the mould is filled with synthetic monomers such as poly(methyl methacrylate) forming a core. The boundary of skirt/core forms an Interpenetrating network and the core is optionally covered by a bacterial resistant biofilm. The hydrogel skirt comprises biological molecules such as peptides, proteins or collagen. US2011/182968 discloses a corneal prosthesis comprising a core and skirt. The core comprises an interpenetrating network comprising PEG-DA (first network) and methacrylic acid (second network) whereas the skirt is hydrogel based and can contain biomolecules linked to it. Biomolecules such as peptides or collagen can be incorporated into the interpenetrating network of the core by forming acrylate-PEG-peptide monomers which can then be linked to PEG-DA of the first network and acrylates of the second network of the core. Myung et al (2007) discloses artificial corneas comprising a central core composed of a poly (ethylene glycol)/poly(acrylic acid) (PEG/PAA) double network with collagen type I tethered to its surface, and a micro-perforated PHEA hydrogel skirt also modified with collagen. The interpenetrating micro-perforated skirt promotes stromal tissue integration whereas the double network core supports surface epithelialization. US2014/0142200 discloses a double-crosslinked, transparent collagen material for use as an ophthalmic device, wherein the collagen is diafiltered, lyophilised, re-dissolved and homogenized and non-fibrillar to reduce small molecule contaminants and subsequently obtaining accurate collagen concentrations essential for an efficient cross-linking method.

Although collagen based interpenetrating network hydrogels are advantageous over synthetic interpenetrating network hydrogels by allowing superior cell adhesion and migration, the production of recombinant collagen is exceedingly expensive making it a less suitable alternative when considering mass production of artificial corneas. Additionally, the production of an artificial cornea comprising skirt and core structure requires several steps thus increasing the cost. Moreover, none of the above attempts to provide a replacement cornea has successfully fully integrated the artificial implant that replaces a damaged or diseased cornea with a fully functional artificial cornea. To date, clinically used prostheses are non-immune, compatible and necessitate live-long immunosupression. Furthermore, increased intraocular pressure leading to glaucoma is a severe side effect that often necessitates co-implantation of a shunt to prevent glaucoma; [see Management of Glaucoma Following Boston Keratoprosthesis: Gargi Khare Vora, Kathryn A Colby European Ophthalmic Review, 2012;6(4): 214-7.

In our co-pending PCT applications, WO2015/032985, WO2015/055661 and WO2015/055656 we disclose a hydrogel, a modified hydrogel and a corneal implant respectively. The content of each PCT application is incorporated by reference in their entirety.

This disclosure relates to a hydrogel comprising a novel collagen mimetic peptide (which can also be described as a collagen-like peptide) that interlinks to form a network, which allows migration of cells and vessel ingrowth aiding regeneration into the surrounding tissue minimising the risk of rejection when used in a corneal implant. Moreover, the artificial cornea comprises a core that prevents cell and vessel ingrowth so maintaining optimal transparency. The use of the novel collagen mimetic peptide forming the network of the hydrogel is advantageous as it allows greater flexibility converting an inert polymeric backbone (plastic or biopolymer such as silk). It also significantly reduces the costs of producing artificial corneas compared to those made from recombinant human collagen due to reduction of the purification steps; and compared to extracted animal source polymers such as collagen, as well as the costs of batch-to-batch testing for pathogens to prevent transmission in extracted materials. The device is of substantial mechanical strength and elasticity allowing additional surface modification. Kits allowing tailor made skirt core matrices are also disclosed.

STATEMENT OF THE INVENTION

According to an aspect of the invention there is provided a peptide comprising an amino acid sequence wherein said peptide comprises at least four amino acid motifs represented in the following formula:

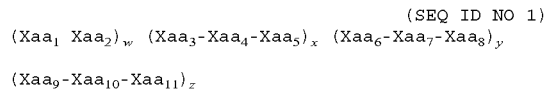

(SEQ ID NO 1)

$(Xaa_1\ Xaa_2)_w$ is a first amino acid motif wherein $Xaa_1$ is a thiol containing amino acid and $Xaa_2$ is a glycine amino acid wherein said $w$ comprises at least one repeat of said first motif, $(Xaa_3-Xaa_4-Xaa_5)_x$ is a second amino acid motif wherein $Xaa_3$ is proline, $Xaa_4$ is lysine, $Xaa_5$ is glycine wherein $x$ comprises 1-4 repeats of said second amino acid motif, $(Xaa_6-Xaa_7-Xaa_8)_y$ is a third amino acid motif wherein $Xaa_6$ is proline, $Xaa_7$ is hydroxyproline, $Xaa_8$ is glycine wherein $y$ comprises 1-4 repeats of said third amino acid motif; and $(Xaa_9-Xaa_{10}-Xaa_{11})$ is a fourth amino acid motif wherein $Xaa_9$ is aspartic acid or glutamic acid, $Xaa_{10}$ is hydroxyproline, $Xaa_{11}$ is glycine wherein z comprises 1-4 repeats of said fourth amino acid motif.

In a preferred embodiment of the invention said thiol containing amino acid is cysteine.

In an alternative embodiment of the invention $Xaa_2$ comprises more than one glycine amino acid residue, for example 1, 2, 3 or 4 glycine amino acid residues.

In a preferred embodiment of the invention said first amino acid motif comprises more than 1 repeat; preferably said peptide comprises 1, 2, 3 or 4 repeats of said first amino acid motif.

In a preferred embodiment of the invention said peptide comprises at least 1, 2, 3 or 4 repeats of said second amino acid motif.

In a preferred embodiment of the invention said peptide comprises at least 1, 2, 3 or 4 repeats of said third amino acid motif.

In a further preferred embodiment of the invention said peptide comprises at least 1, 2, 3 or 4 repeats of said fourth amino acid motif.

In a preferred embodiment of then invention said peptide comprise the amino acid sequence $Xaa_1$-Gly-(Pro-Lys-Gly)$_4$(Pro-Hyp-Gly)$_4$(Asp-Hyp-Gly)$_4$ (SEQ ID NO 2)

wherein $Xaa_1$ is a natural or modified thiol containing amino acid.

In a preferred embodiment of the invention said peptide comprises the amino acid sequence Cys-Gly-(Pro-Lys-Gly)$_4$(Pro-Hyp-Gly)$_4$(Asp-Hyp-Gly)$_4$ (SEQ ID NO 3)

wherein said peptide is a collagen mimetic peptide.

In a preferred embodiment of the invention said peptide comprises the amino acid sequence Cys-Gly-(Pro-Lys-Gly)$_4$(Pro-Hyp-Gly)$_4$(Glu-Hyp-Gly)$_4$ (SEQ ID NO 4)

wherein said peptide is a collagen mimetic peptide.

In a preferred embodiment of the invention said peptide comprises an amino acid sequence selected from the group consisting of:

Cys-Gly-(Pro-Lys-Gly)$_4$(Pro-Hyp-Gly)$_4$(Asp-Hyp-Gly)$_4$-Gly-Gly-(Pro-Lys-Gly)$_4$(Pro-Hyp-Gly)$_4$(Asp-Hyp-Gly)$_4$; (SEQ ID NO 5)

Cys-Gly-Gly-Gly-Gly-(Pro-Lys-Gly)$_4$(Pro-Hyp-Gly)$_4$(Asp-Hyp-Gly)$_4$; (SEQ ID NO 6)

Cys-Gly-(Pro-Lys-Gly)$_4$(Pro-Hyp-Gly)$_4$(Asp-Hyp-Gly)$_4$-Arg-Gly-Asp-Ser-Pro-Gly (SEQ ID NO 7); or

Cys-Gly-(Pro-Lys-Gly)$_4$(Pro-Hyp-Gly)$_4$(Asp-Hyp-Gly)$_4$-Ile-Lys-Val-Ala-Val-Gly (SEQ ID NO 8)

wherein said peptide is a collagen mimetic peptide.

In a preferred embodiment of the invention said peptide is at least 11 amino acids in length; preferably said peptide comprises 11 to 38 amino acids.

In a preferred embodiment of the invention said peptide is greater than 38 amino acids in length; preferably, between 38 amino acids and 100 amino acids in length. In an alternative embodiment said peptide is at up to 500 amino acids in length.

In a preferred embodiment of the invention said peptide is derivatized by chemical modification to provide one or more reactive groups.

In a preferred embodiment of the invention said peptide is modified by addition of one or more functional groups selected from the group consisting of: thiol, methacrylate or acrylate functional groups.

In a preferred embodiment of the invention said modified peptide comprises polyethylene glycol; preferably polyethylene glycol-maleimide or polyethylene glycol diacrylate or polyethylene glycol methacrylate.

Preferably said polyethylene glycol-maleimide is at least 2, 4, 6 or 8 arm polyethylene glycol-maleimide.

Preferably, said polyethylene glycol-maleimide is more than an 8 arm polyethylene glycol-maleimide.

According to a further aspect of the invention there is provided a hydrogel comprising: a plurality of modified collagen mimetic peptides according to the invention chemically cross linked into a network.

In a preferred embodiment said modified collagen mimetic peptide is activated via N-ethyl-N'-[3-dimethylaminopropyl] carbodiimide/N-hydroxy succinimide (EDC/NHS).

In a preferred embodiment said modified collagen mimetic peptide is crosslinked using initiator for example riboflavin.

In a preferred embodiment of the invention said hydrogel comprises one or more natural or synthetic biopolymers chemically cross linked to said network.

In a preferred embodiment of the invention said natural polymer is a collagen.

In a preferred embodiment of the invention said collagen is selected from the group consisting of: collagen I, collagen II, collagen III, collagen IV or collagen V, or mixtures thereof.

In an alternative preferred embodiment of the invention said natural polymer is selected from the group consisting of: fibrin, cell-interactive proteins and other biopolymers, for example laminin, fibronectin, hyaluronic acid, chitosan, collagen mimetic peptides of different sequence to the collagen mimetic peptide according to the invention.

In a preferred embodiment of the invention said synthetic polymer is selected from the group consisting of: functionalized polyethylene glycol (PEG), polyvinyl alcohol (PVA), polyethylene glycol-diacrylate (PEGDA), PEG methacrylate (PEGMA), poly(hydroxyethyl methacrylate) (pHEMA), polyethylene glycol methyl ether methacrylate (PEGMEM), poly(pentaerythritol triacrylate) or poly(N-isopropylacryl amide) (PNIPAAm).

In a further preferred embodiment of the invention said network comprises a photoinitiator, for example Irgacure 2959.

In a further preferred embodiment of the invention said network comprises a photoinitiator, for example riboflavin.

In a preferred embodiment of the invention said network is photo-crosslinked.

In an alternative preferred embodiment of the invention said modified collagen mimetic peptide is crosslinked using glutaraldehyde.

In a preferred embodiment of the invention said hydrogel is substantially transparent and allows a light transmission of at least 80 or 90% of light in the range of 400-700 nm.

In a preferred embodiment of the invention the total concentration of polymers in the hydrogel is at least 2 weight % or more.

According to a further aspect of the invention there is provided a method of manufacturing a hydrogel comprising the steps:
  i) providing a preparation comprising a modified peptide according to the invention;
  ii) providing a preparation comprising one or more biocompatible polymers and/or monomers wherein said polymers are provided with one or more functional groups;
  iii) combining preparations i) and ii) to provide a reaction mixture and contacting said reaction mixture with a crosslinking agent.
  iv) incubating the reaction mixture to crosslink said modified peptide with one or more biocompatible polymers and/or monomers to provide a cross-linked network.

In a preferred method of the invention said functional groups are selected from the group consisting of: thiol, acrylate and/or methacrylate, or synthetic monomers having thiol, acrylate and/or methacrylate functional groups.

In a preferred method of the invention said mixture of first and second preparation has a total polymer concentration of at least 2 weight %; preferably 12 weight %

In a preferred method of the invention said cross-linking agent is a chemical cross-linker.

In an alternative preferred method of the invention said cross-linking agent is a photoinitiator and UV radiation.

In an alternative preferred method of the invention said cross-linking agent is glutaraldehyde.

According to a further aspect of the invention there is provided a hydrogel according to the invention wherein said hydrogel is modified to provide a uniformly functionalized or patterned surface to which cells and/or biocompatible or biologically/chemically active polymers/monomers adhere to modulate cell contact.

In a preferred embodiment of the invention said modulation is enhancement of cell adhesion and proliferation.

In an alternative embodiment of the invention said modulation is inhibition of cell adhesion.

In the present disclosure the hydrogel is formed by reacting firstly functionalised PEG optionally comprising multiple arms with a modified collagen mimetic peptide. The pegylated peptides are then subsequently cross linked by either chemical activation or UV crosslinking using a photo initiator. Further polymers can then be crosslinked again using chemical activation or a UV photoinitiator optionally forming a second network if desired. Optionally, further functionalization of the hydrogel surface can be achieved by providing a PEG-MA coating or chemical activation of the peptide carbonyl or other groups.

In the present disclosure the term "pattern" encompasses physical, chemical, or topographic, 2D or 3D, patterns. The present disclosure includes "surface modifying" the hydrogel according to the invention wherein the hydrogel has mechanical properties that allows such modifications. In order for the hydrogels to be surface modified according to the present invention it is preferable if the hydrogel has an elastic modulus of at least 1 MPa or at least 2 MPa, or at least 3 MPa, or at least 4 MPa, or at least 5 MPa. The hydrogel according to the present invention contains at least 80 wt % water, or at least 85 wt % water, or at least 90 wt % water, for example 85-90 wt % water.

In a further preferred embodiment of the invention the hydrogel has an elastic modulus of at least 0.1 MPa or at least 1 MPa or at least 2 MPa or at least 3 MPa, or at least 4 MPa, or at least 5 MPa. Preferably, the elastic modulus is at least 0.18 MPa.

The hydrogel according to the invention combined with surface modification/patterning enhances for example tissue regenerative properties of the hydrogel but may also be used for construction of in vitro tissue models, arrays or tissue-on-a-chip devices. For example, fibronectin patterns of relatively narrow stripes/lines, said stripes may further stimulate epithelial cell proliferation on a material that supports tissue regeneration. To use contact printing, photolithography on hydrogels is known. However, prior art discloses difficulties to produce well defined patterns and the methods are usually not suitable for large scale production. The present disclosure illustrates that even highly aqueous hydrogel material may be used for contact printing or photolithography for example to prepare a surface pattern on the material. Prior art have shown that when photolithography is applied on gels in a dry collapsed state the pattern may be distorted/damaged when the gels subsequently are rehydrated in buffer. Moreover, performing photolithography in water is expensive and technically difficult, especially on other hydrogel materials having ill-defined surfaces, and not compatible with most of the production facilities. Instead of such complicated processes, by using a material that has a well-defined surface and physically withstands contact printing or photolithography the present disclosure makes it possible to prepare hydrogels containing 2D patterns/3D patterns in large scale production.

According to a further aspect of the invention there is provided a method for the modification of a hydrogel comprising:
 i) providing a hydrogel according to the invention;
 ii) applying to the surface of said hydrogel one or more monomeric or polymeric agents to modify the surface of the hydrogel; and/or
 iii) treating the applied surface compounds by microcontact printing or photolithography or inkjet printing, or any other fabrication technique in order to create a pattern of said surface compounds.

In a preferred method of the invention said agents are selected from the group consisting of: polyethylene glycol (PEG)-acrylate polymer/monomers, PEG-methacrylate polymer/monomers, other acrylate, methacrylate, carboxyl, amino, amide, epoxide, hydroxyl, cyano, nitride, sulfonamido, acetylenyl, alkene, esters like imidoesters(N-hydroxysuccinimide ester) or pentafluorphenol ester or other, azide, thiol, maleimide, functionalized PEG derivatives, any bifunctional or multifunctional compounds, drugs, bioactive substances, biological molecules including proteins or peptides to said surface.

In a preferred embodiment of the invention said agent is a cell adhesion or cell modulating protein.

In a preferred method of the invention said agent is selected from the group consisting of: fibronectin, laminin, vitronectin or peptide motifs derived from these.

In a preferred method of the invention the pattern is in the shape of lines or dots, or any other geometrical figures having a width or diameter or any other geometrical parameter of at least 10 nm or more.

In a preferred method of the invention the width or diameter or any other geometrical figures of the pattern is from 1 µm or more.

According to an aspect of the invention there is provided a modified hydrogel obtained or obtainable by the method according to the invention.

In a preferred embodiment of the invention said hydrogel or modified hydrogel comprises at least one cell type.

In a preferred embodiment of the invention said cell type is a mammalian cell; preferably a human cell, for example an epithelial cell or mesenchymal-like stromal cells.

In a preferred embodiment of the invention said cell type is a stem cell.

The term "stem cell" represents a generic group of undifferentiated cells that possess the capacity for self-renewal while retaining varying potentials to form differentiated cells and tissues. Stem cells can be pluripotent or multipotent. A pluripotent stem cell is a cell that has the ability to form all tissues found in an intact organism although the pluripotent stem cell cannot form an intact organism. Furthermore, it is known that human somatic cells can be re-programmed to an undifferentiated state similar to an embryonic stem cell. For example, WO2007/069666, the content of which is incorporated by reference in its entirety, describes re-programming of differentiated cells (e.g. mouse fibroblast cells) without the need to use embryonic stem cells.

A multipotent cell has a restricted ability to form differentiated cells and tissues. Typically, adult stem cells are multipotent stem cells and are the precursor stem cells or lineage restricted stem cells that have the ability to form some cells or tissues and replenish senescing or damaged cells/tissues. Generally they cannot form all tissues found in an organism, although some reports have claimed a greater potential for such 'adult' stem cells than originally thought. Examples of multipotent stem cells include mesenchymal stem cells. Mesenchymal stem cells differentiate into a variety of cell types that include osteoblasts, chondrocytes, myocytes, adipocytes and neurones. Typically, mesenchymal stem cells are obtained from bone marrow. Currently, stem cell therapies are exploring different sources of pluripotent and multipotent stem cells and cell culture conditions to efficiently differentiate stem cells into cells and tissues suitable for use in tissue repair.

In a preferred embodiment of the invention said stem cell is a corneal stem cell or progenitor cell.

In a preferred embodiment of the invention said stem cell is a corneal endothelial cell or progenitor cell.

According to a further aspect of the invention there is provided a corneal implant comprising a hydrogel according to the invention.

In a preferred embodiment of the invention said corneal implant comprises a matrix part comprising a hydrogel according to the invention and a core part wherein the core part is substantially centrally located in the matrix part and comprises polymerized olefinic or UV polymerizable monomers, or a mixture thereof, the hydrogel of the matrix material and one or more antifouling polymers/agents characterised in that the core part is substantially transparent and free of cells/vessels.

In a preferred embodiment of the invention the core material comprises: HEMA and PEGMEM or HEMA and 2-methacryloyloxyethyl phosphorylcholine (MPC).

In a preferred embodiment of the invention said polymerized olefinic or UV polymerizable monomers are selected from the group: methyacrylate, methylmethacrylate, poly methyl methacrylate (PMMA), poly-hydroxyethyl methacrylate (pHEMA), pHEMA-poly ethylene glycol methacrylate or pHEMA-PEGMEM.

In a preferred embodiment of the invention the surface of the matrix material and/or the core material is modified and/or patterned with PEG-MA.

In a preferred embodiment of the invention the surface of the matrix material and/or the core material is activated using NHS/EDC.

In a preferred embodiment of the invention the surface of the matrix material and/or the core material is modified and/or patterned with N-hydroxysulfosuccinimide (NHS), polypeptides such as YIGSR (SEQ ID NO 9), IKVAV (SEQ ID NO 10), RGD, ECM proteins, fibronectin derived peptides, combinations of synergistic peptides, DGEA peptide from collagen, antibodies, glycosaminoglucans, motifs from growth factors, or pharmaceutically active substances.

In a preferred embodiment of the invention the weight ratio of core material is 1 wt % or more, or 5 wt % or more, or 15 wt % or more, or 30 wt % or more, or 50 wt % or more, or 95 wt % or less, or 85 wt % or less, or 75 wt % or less, or 65 wt % or less, or 55 wt % or less, of the total weight of the product.

In a preferred embodiment of the invention the matrix material comprises at least the collagen mimetic peptide according to the invention modified with polyethylene glycol wherein the PEG has 2, 4, 6 or 8 arms; preferably 8 arms.

In a preferred embodiment of the invention the matrix material comprises at least the collagen mimetic peptide according to the invention modified with polyethylene glycol wherein the PEG has more than 8 arms.

In a preferred embodiment of the invention said core material comprises HEMA and/or PEGMEM, or HEMA and/or MPC.

According to a yet further aspect of the invention there is provided a method for the manufacture of an implant according to the invention comprising:
  i) providing a matrix polymer and a cross-linker in a suitable solvent;
  ii) cross-linking the matrix polymer to form the matrix material;
  iii) providing core olefinic monomers or UV polymerizable monomers or polypeptides or a mixtures thereof, and an initiator, optionally in a suitable solvent;
  iv) adding the core olefinic monomers or UV polymerizable monomers or polypeptides, or a mixtures thereof and the initiator to the surface or the body of the matrix material; and
  v) allowing the core olefinic monomers to polymerize for a suitable period of time.

In a preferred method of the invention the olefinic based material is left to diffuse after addition in at least 15 minutes.

In a further preferred method of the invention the curing of said core is obtained during UV radiation using a mask.

According to a further aspect of the invention there is provided an implant according to the invention for use in the repair or replacement of disease or damaged corneal tissue.

According to a further aspect of the invention there is provided a surgical method for the repair or replacement of diseased or damaged corneal tissue in a subject in need of corneal repair or damage comprising:
  i) providing a corneal implant according to the invention;
  ii) attaching the corneal implant to the eye of said subject; and optionally
  iii) providing a protective covering to the repaired eye to facilitate healing.

In a preferred embodiment of the invention said use or surgical method is the repair or replacement of diseased corneal tissue wherein said disease is selected from the group consisting of: Fuchs' Dystrophy, iridocorneal endothelial syndrome, keratoconus, lattice dystrophy, ocular herpes infections, trachoma as examples.

In an alternative embodiment of the invention said use or surgical method is the repair or replacement of damaged corneal tissue wherein said damage is chemical damage, physical injury during sport or during military conflict.

According to a further aspect of the invention there is provided a hydrogel or modified hydrogel according to the invention for use in cell and tissue culture.

According to a further aspect of the invention there is provided a hydrogel or modified hydrogel according to the invention for use in: high-throughput or lab-on-a-chip systems, microscopy and microarray substrates, microfluidic or sampling, separation, purification, analytical tools.

According to a further aspect of the invention there is provided a kit comprising:
  i) a hydrogel or modified hydrogel according to the invention;
  ii) a preparation comprising one or more biocompatible polymers/monomers;
  iii) cross-linking agent[s].

In a preferred embodiment of the invention said biocompatible polymers/monomers cross-linkable.

In a preferred embodiment of the invention said cross-linkable polymer is selected from the group consisting of: methacrylate, methylmethacrylate, poly methyl methacrylate (PMMA), poly-hydroxyethyl methacrylate (pHEMA), pHEMA-poly ethylene glycol methacrylate or pHEMA-PEGMEM.

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Figure 2:
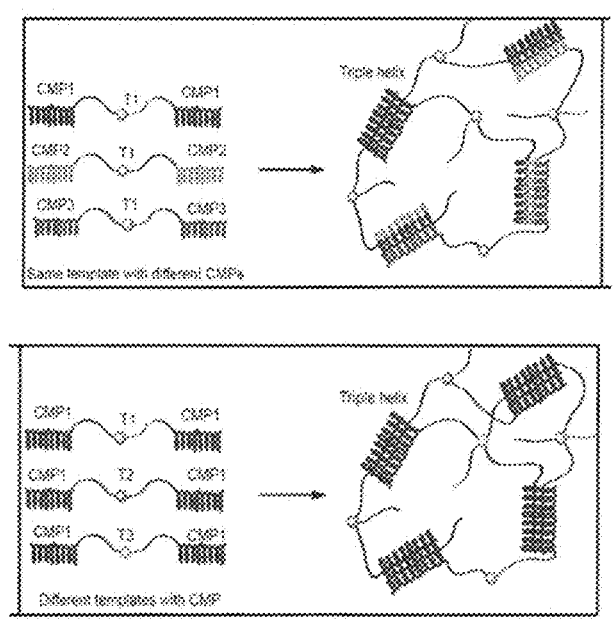
Figure 3:
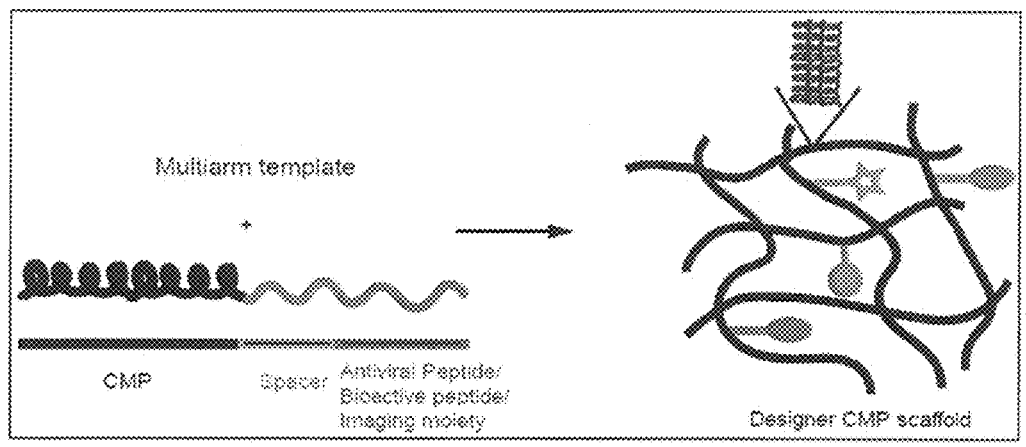
Figure 4:
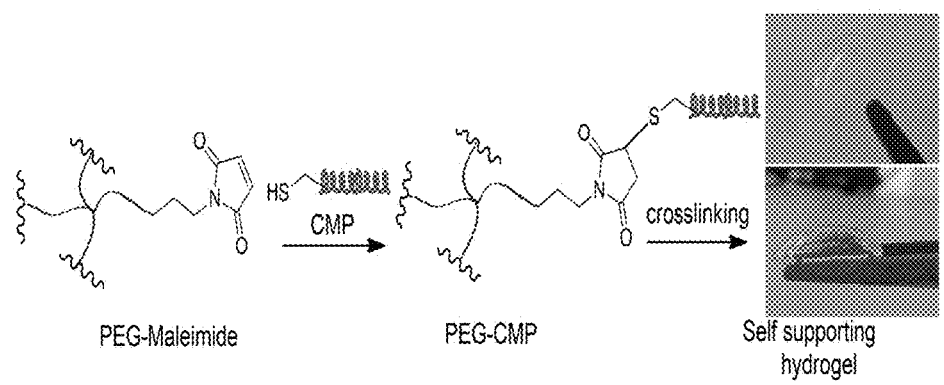
Figure 5:
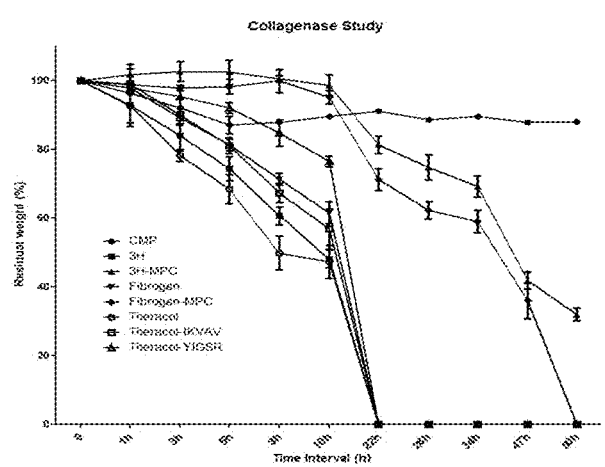
Figure 5:
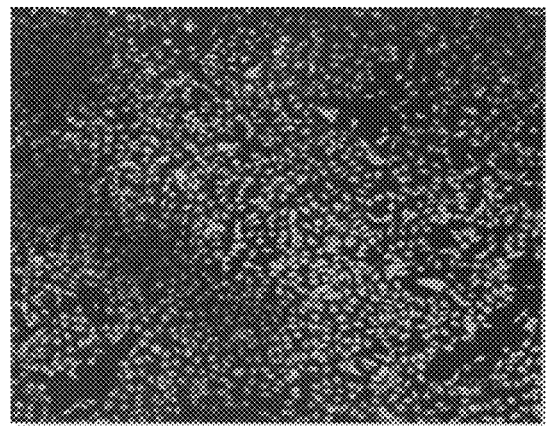

An embodiment of the invention will now be described by example only and with reference to the following figures:

FIG. 1: illustrates a schematic for fabrication of template assisted triple helical polypeptides;

FIG. 2: illustrates a schematic for self-assembling via hetero-association of triple helix;

FIG. 3: illustrates a schematic model of scaffold functionalization;

FIG. 4: illustrates synthesis of CMP-PEG self-supporting hydrogel;

FIG. 5: Hydrogel enzymatic stability (FIG. 5A) compared with EDC/NHS cross linked human recombinant collagen hydrogels; FIG. 5B- illustrates hydrogel supported the growth and proliferation of human corneal epithelial cells.

Figure 6:
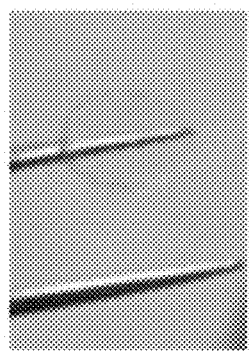
Figure 6:
Figure 7:
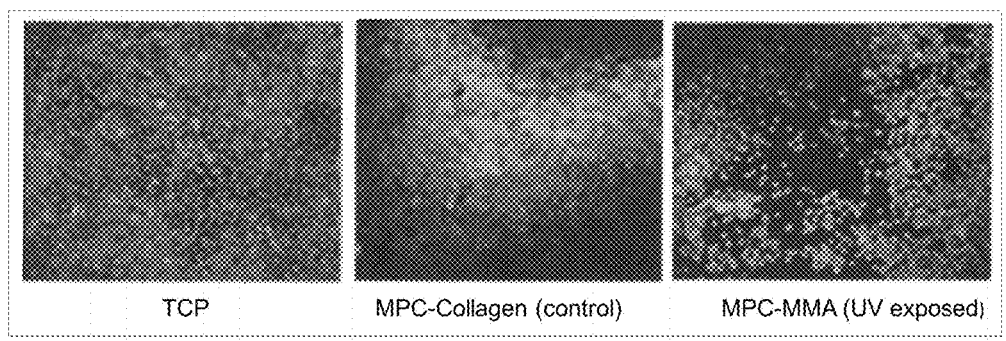
Figure 8:
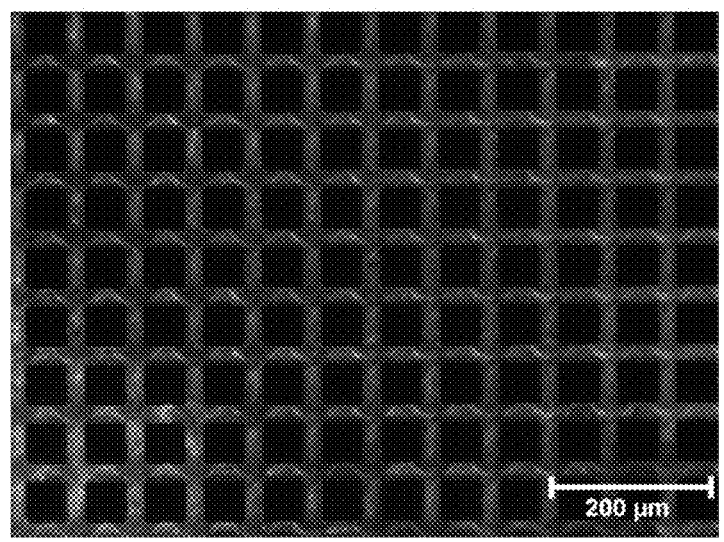
Figure 9:
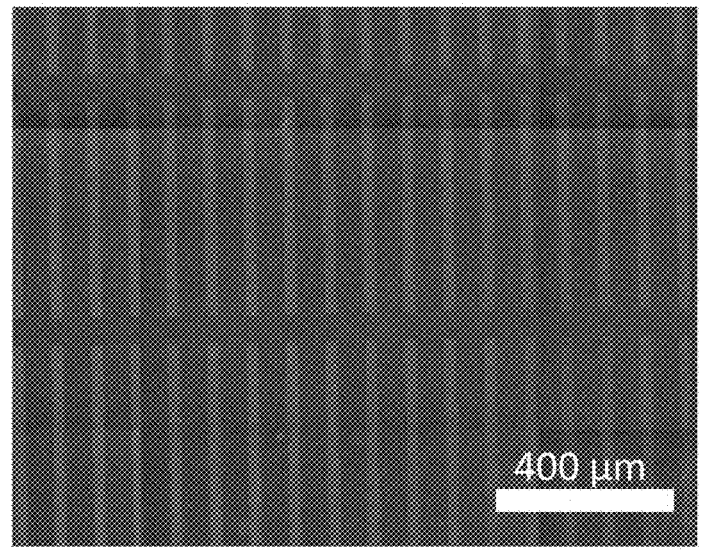
Figure 9:
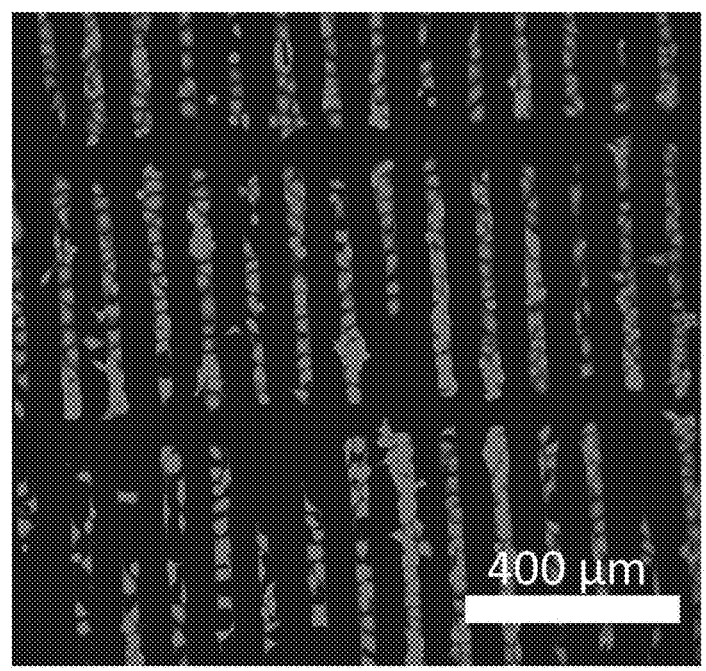
Figure 9:
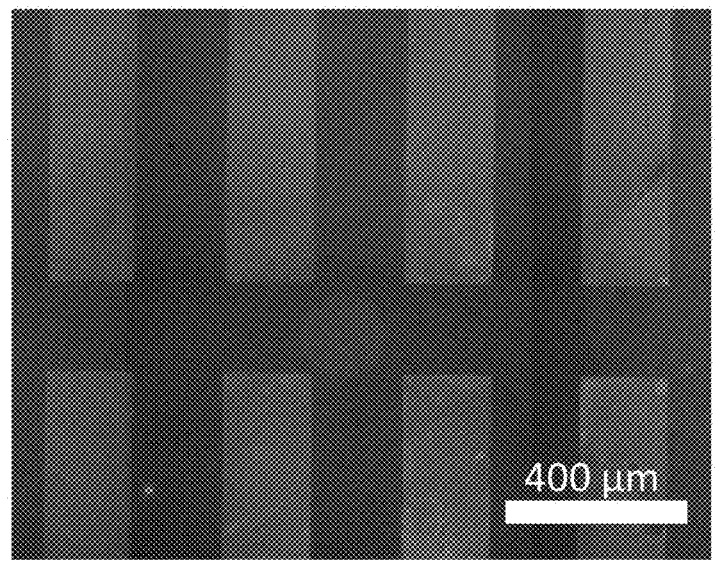
Figure 9:
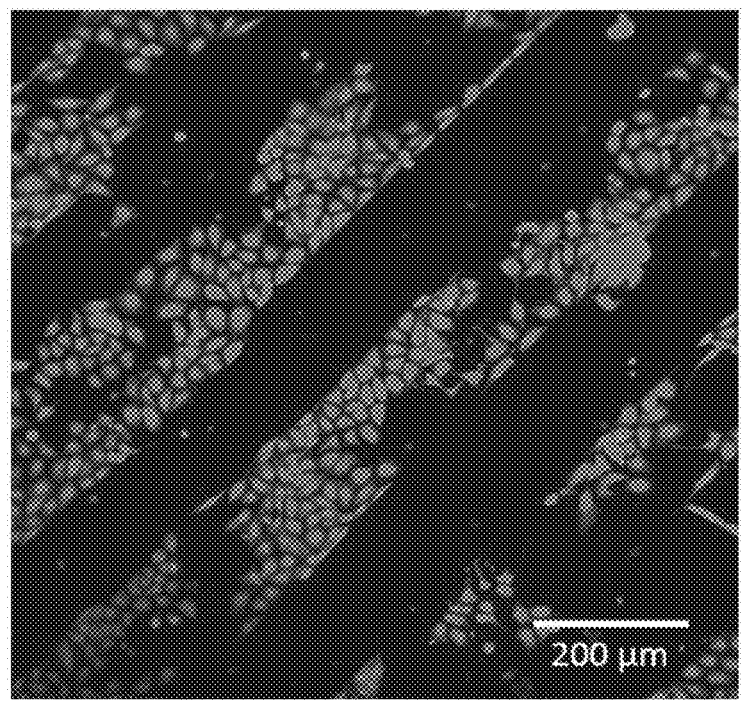
Figure 10:
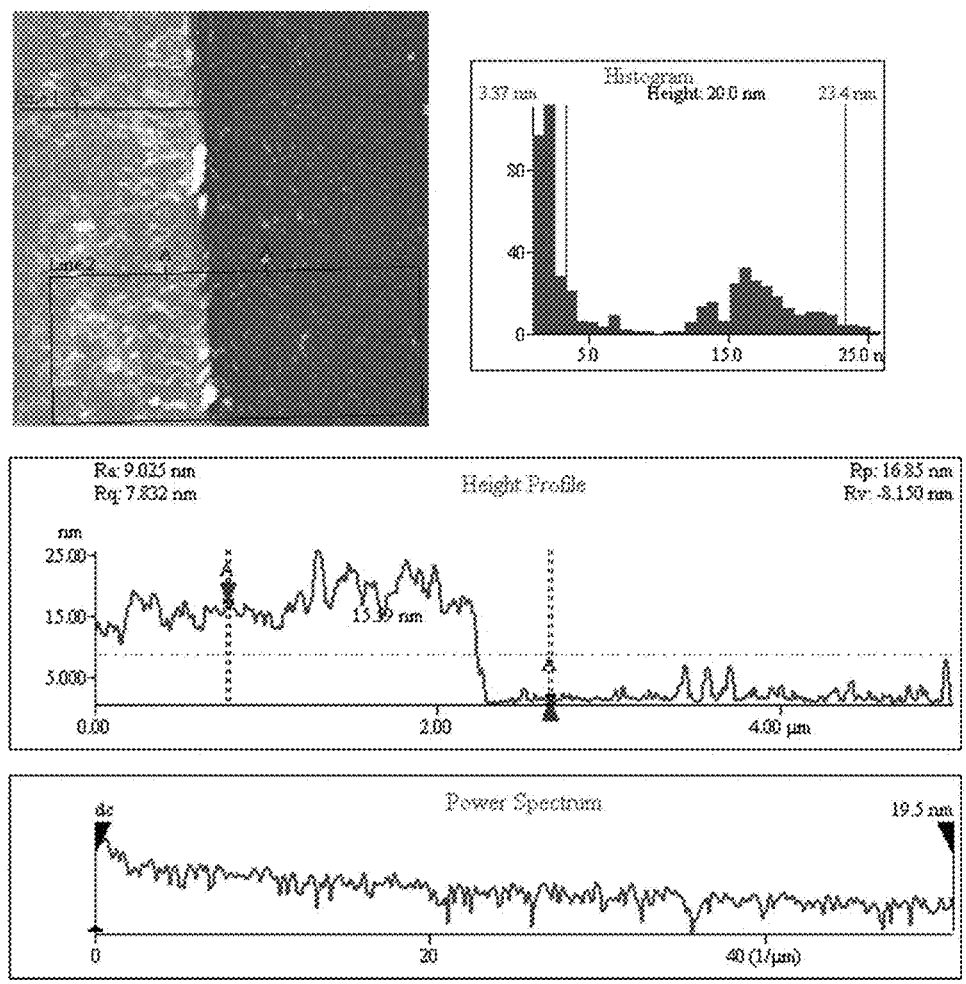
Figure 10:
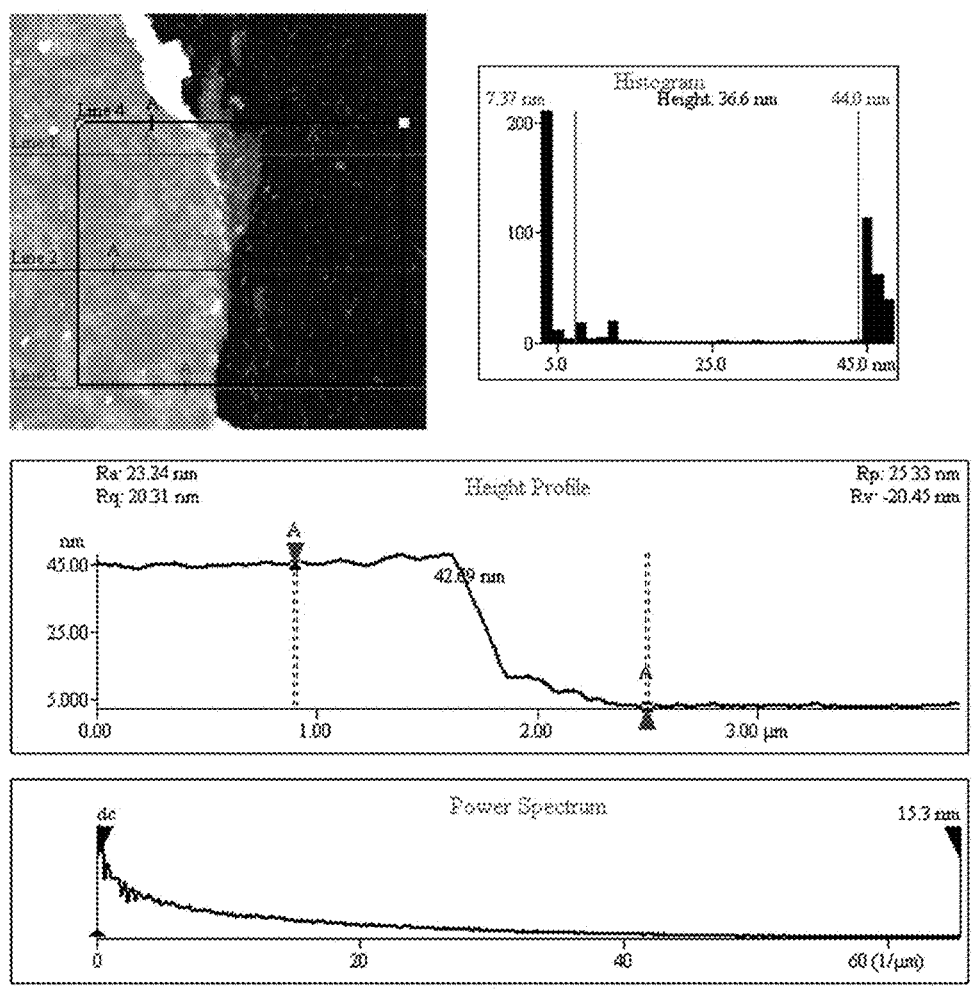
Figure 10:
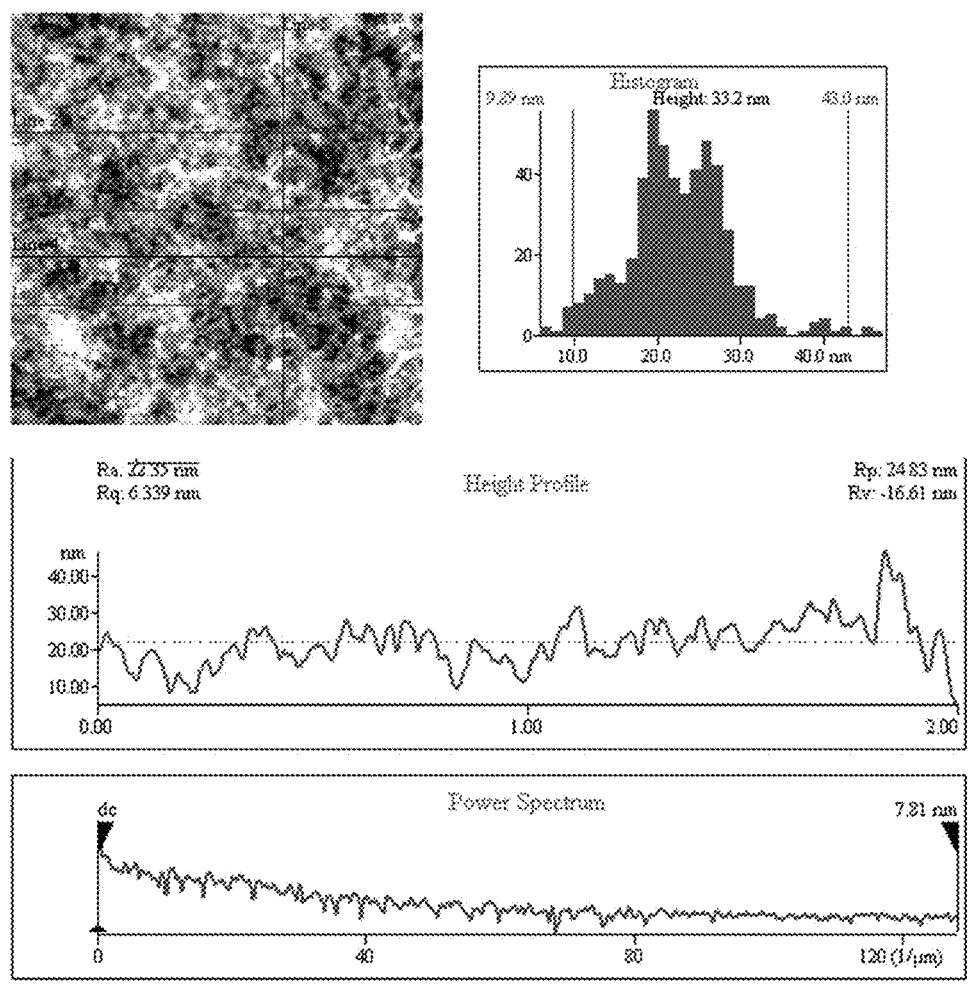
Figure 10:
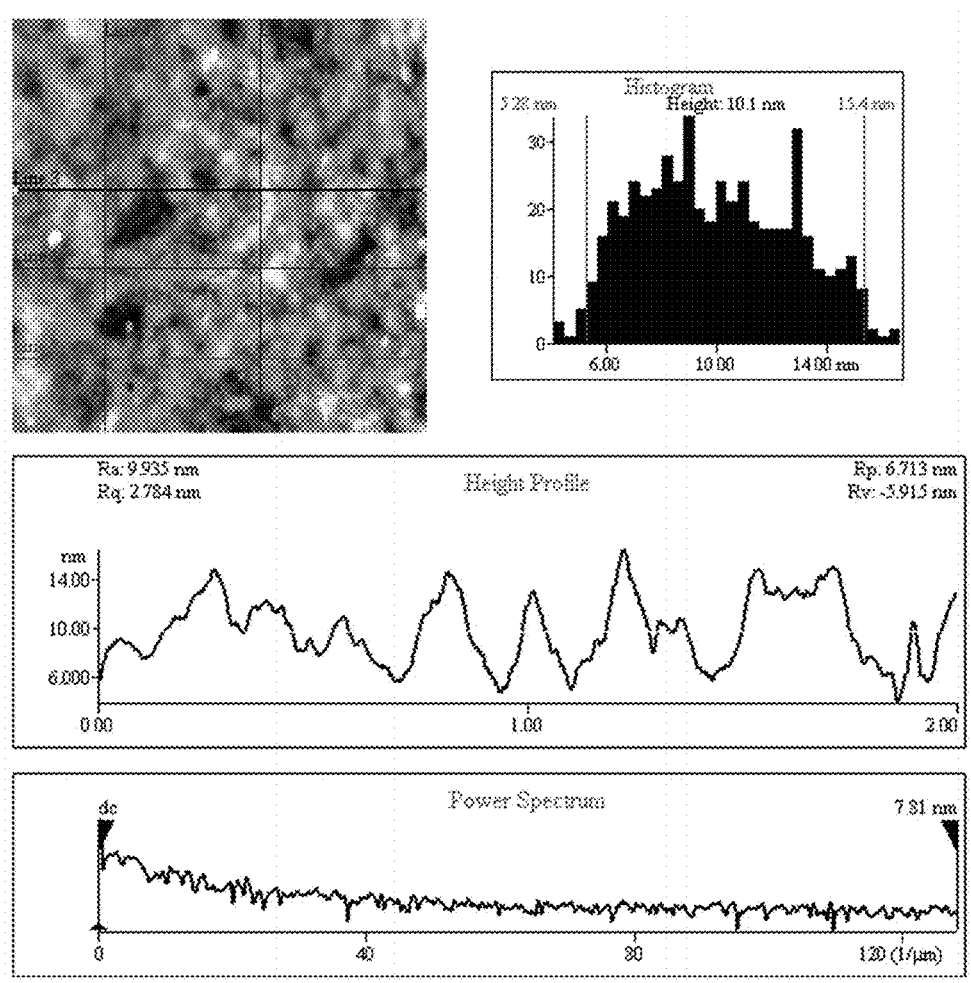
Figure 11:
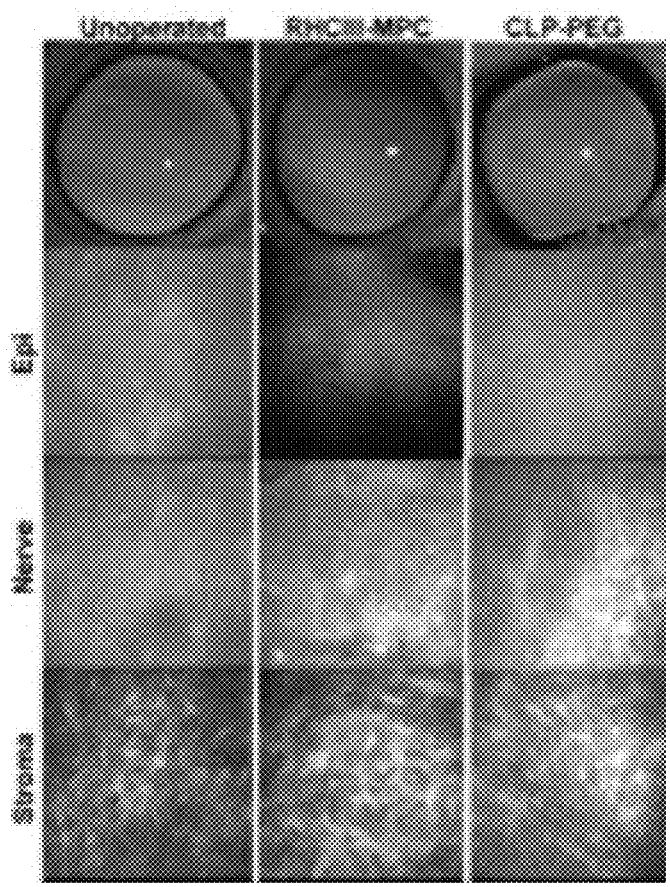
Figure 12:
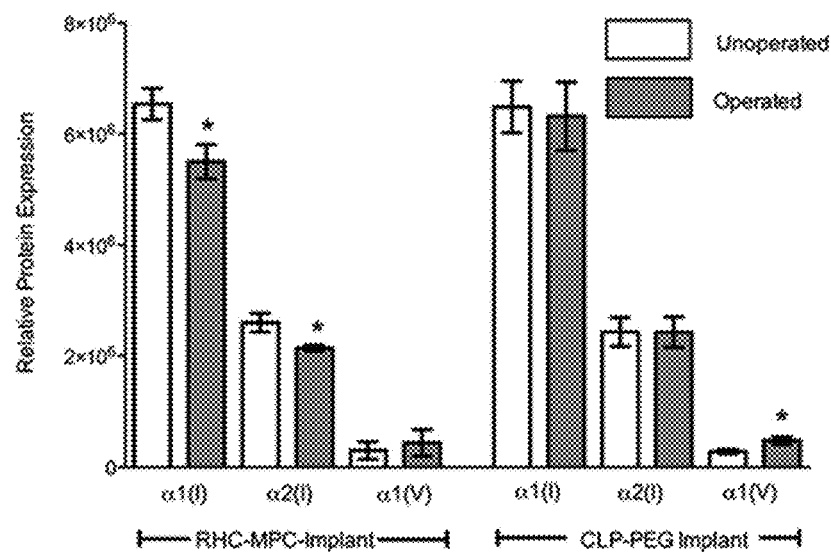

FIG. 6: illustrates collagen-MPC hydrogel and; collagen-MPC hydrogel with central poly methyl methacrylate core serving as an optic;

FIG. 7: illustrates corneal epithelial cell culture on the MPC-MMA surface (images taken after 3 days of culture);

FIG. 8: illustrates fluorescence micrograph showing visualization of a biotin-terminated pattern;

FIG. 9: FIG. 9A illustrates human fibronectin (traces of BSA-TR®) patterns on MPC collagen hydrogel: the line width 30 μm, space in-between 60 μm. FIG. 9B Corneal epithelium cells on 30 μm-wide line patterns on MPC collagen hydrogel; FIG. 9C Human fibronectin (trace of BSA-TR®) patterns on MPC collagen, the line width 200 µm, spacing 200 µm. FIG. 9D Corneal epithelium cells on 200 µm line patterns on MPC collagen;

FIG. 10: Atomic force microscopy (AFM) analysis of a collagen film (supported on a Si wafer) modified with a layer of PEG hydrogel. FIG. 10A section analysis of an AFM topography image of an unmodified collagen film spin-coated on Si wafer. FIG. 10B the same sample after PEG hydrogel photografting. FIG. 10C surface roughness analysis of unmodified collagen film, like in FIG. 10A. FIG. 10D surface roughness analysis of the PEG-hydrogel coating on a collagen film;

FIG. 11: is a photographic image to illustrate a comparison between CMP/CLP-PEG implants with recombinant human collagen (RHC)-MPC implants;

FIG. 12 illustrates the 12 month results of RHCIII-MPC versus CLP-PEG corneas, showing similar performance in epithelial overgrowth and in growth of nerves and stromal cells. Both regenerated corneas show comparable feasters to the control, unoperated healthy cornea. Analysis of normalized, relative protein content shows that the levels of α1(I) and α2(I) in CLP-PEG implanted corneas were similar to that of the control healthy corneas (no statistical significance) while the level of α1(V) however was higher than that of the control ($P \leq 0.05$, indicated by). In RHC-MPC implanted corneas, levels of both α1(I) and α2(I) were significantly lower than in the unoperated controls (*), while α1(V) were similar. No differences were observed between RHCIII-MPC and CLP-PEG implants in general.

Figure 13:
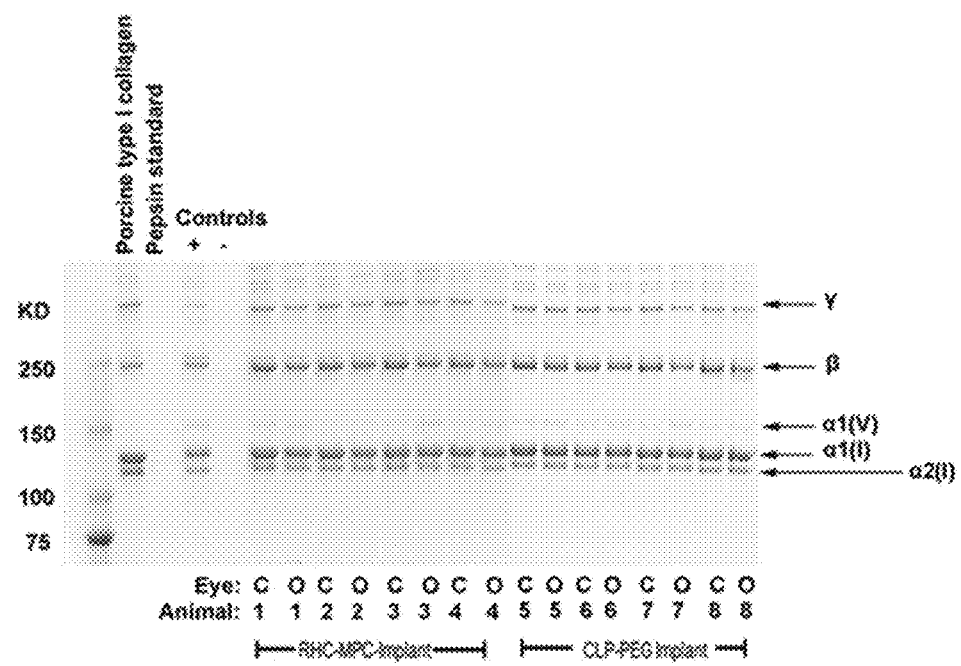

FIG. 13 illustrates SDS-PAGE profiles of pepsin soluble proteins extracted from the implant region of operated corneas (O), after separation on a 3-8% gradient Tris-acetate gel. Controls comprise identically processed proteins from the unoperated control cornea (C), porcine collagen type 1, pepsin standard, pepsin digest from rat cornea (+) pepsin digest from an unused rhCIII implant (−). This shows that both RHCIII-MPC implanted eyes (animals 1-4) and CLP-PEG implanted eyes (animals 5-8) were remodelled to show type I and type V collagen instead of the initial type III collagen.

Figure 14:
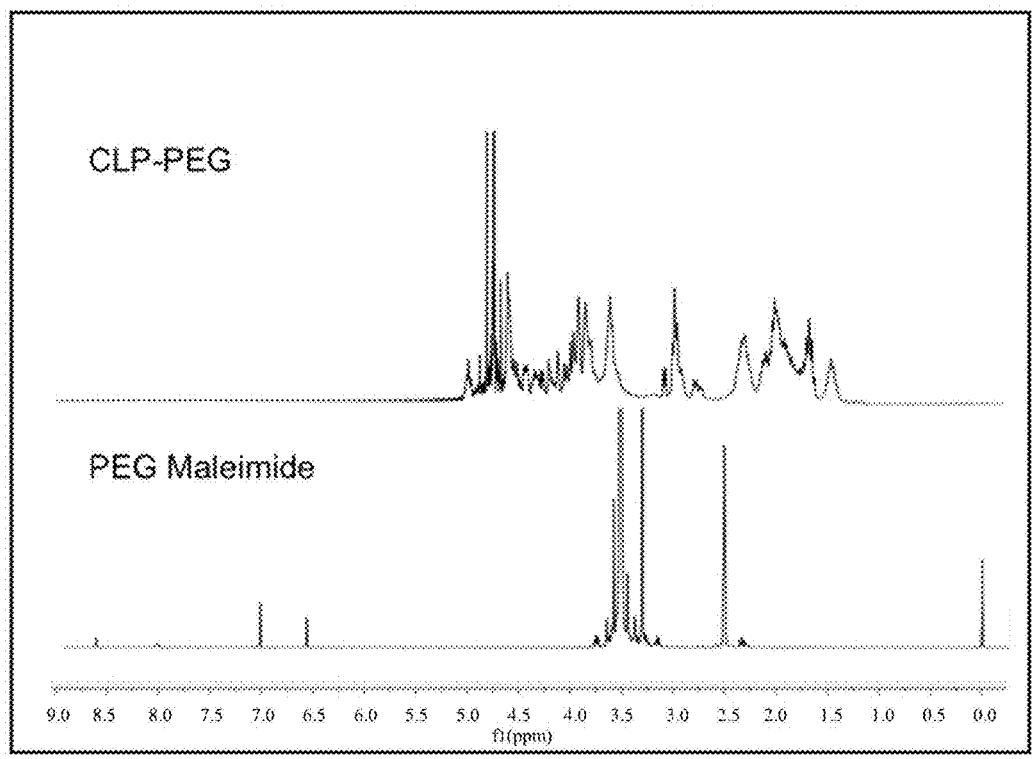
Figure 14:
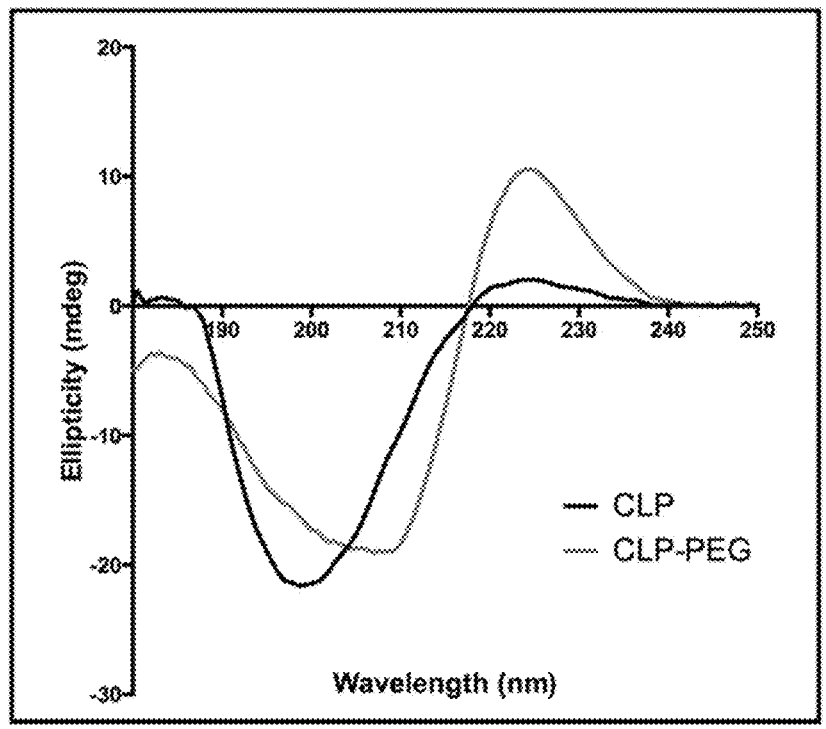
Figure 14:
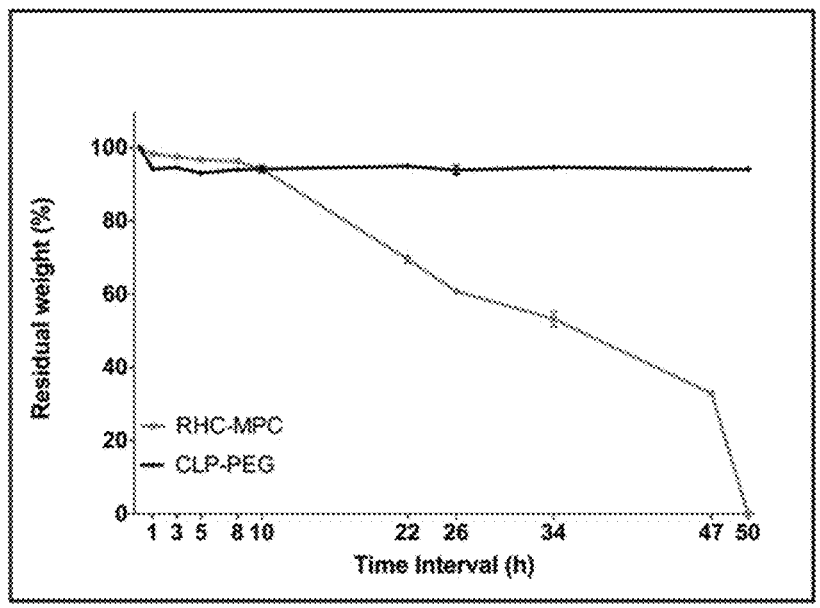
Figure 14:
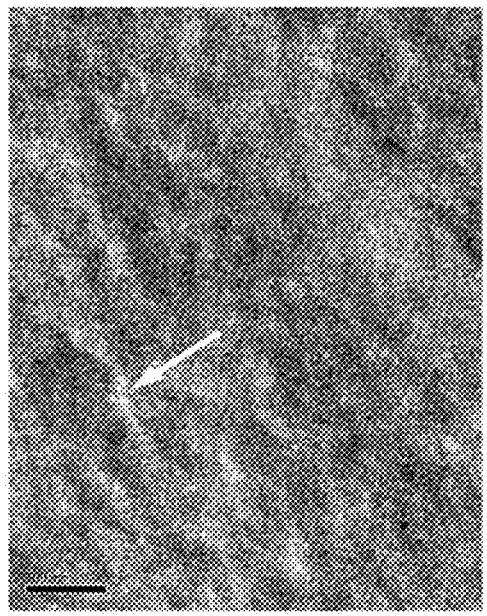
Figure 14:
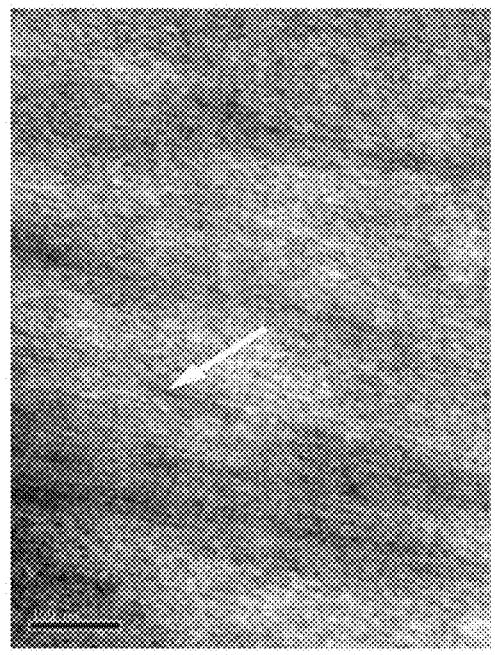
Figure 14:
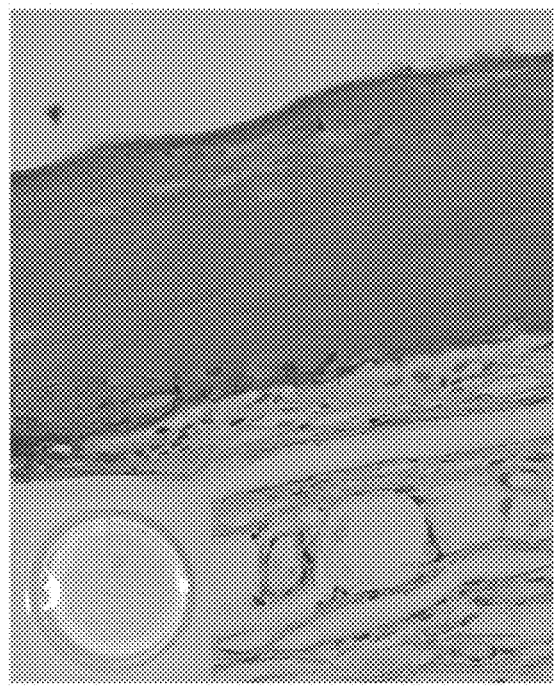

FIG. 14. Illustrates the characterisation of CLP-PRG implants. Characterization of CLP-PEG implants. (FIG. 14A) NMR spectra of CLP-PEG and PEG maleimide, showing maleimide peaks at δ 6.5-7.0 ppm that disappeared after conjugation of CLP. (FIG. 14B) CD spectra of CLP and CLP-PEG confirming their collagen-like triple helical secondary structure. The larger positive peak at 221 nm for CLP-PEG compared to CLP only shows a higher order triple helical propensity facilitated by the presence of PEG. (FIG. 14C) CLP-PEG is resistant to in vitro biodegradation in high concentrations of collagenase, compared to RHC-MPC, which degraded completely over 50 hours. (FIG. 14D) High power TEM images reveals fibril-like structures in CLP-PEG hydrogels, comparable fibrils observed in full-length RHC (FIG. 14E); Bars, 100 nm. (FIG. 14F) Representative H&E stained section of CLP-PEG hydrogels implanted subcutaneously into rats for 90 days, showing a smooth, intact material edge and absence of heavy fibrotic tissue or inflammatory cells. Inset: intact sample retrieved after implantation. Bar, 50 µm.

Figure 15:
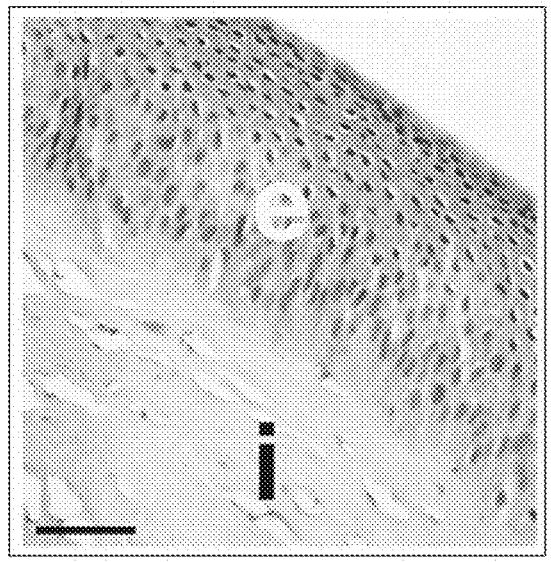
Figure 15:
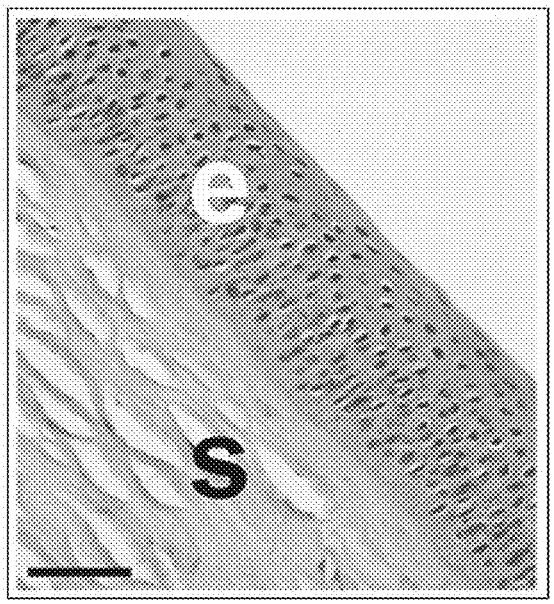
Figure 15:
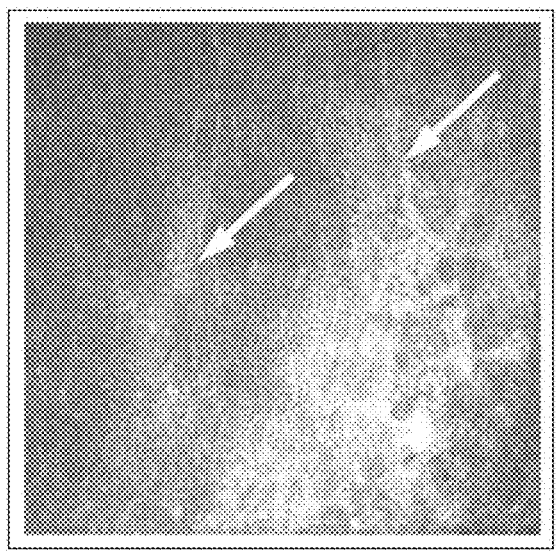
Figure 15:
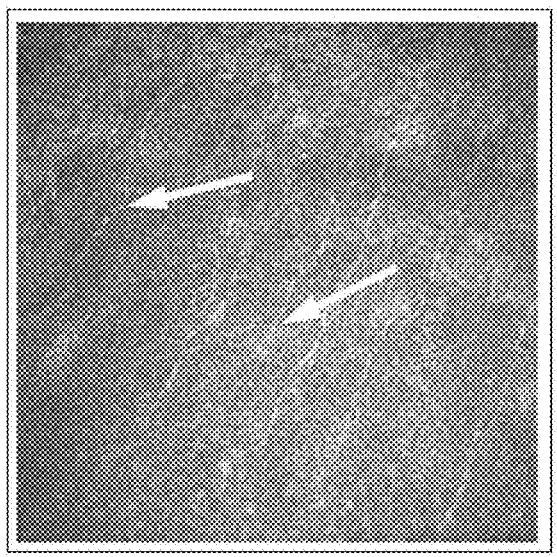
Figure 15:
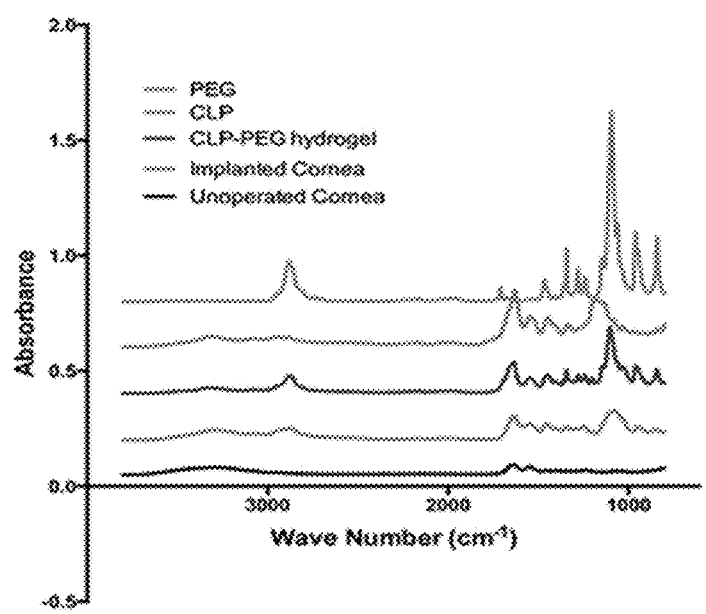

FIG. 15. (FIG. 15A) H&E staining of a representative regenerated CLP-PEG neo-cornea compared to a healthy control cornea (FIG. 15B), showing similar morphology. e, epithelium; s, stroma; i, implant. Bar, 50 µm. FIG. 15C-in vivo confocal microscopy shows the regenerated nerve (arrows) in CLP-PEG cornea, that follow a parallel pattern similar to that of the unoperated cornea (FIG. 15D), (FIG. 15E) FTIR analysis of regenerated pig neo-corneas 12 months after grafting with CLP-PEG implants shows the presence of both CLP and PEG; and FIG. 16. In vivo confocal images of pig corneas grafted with CLP-PEG implants and unoperated control corneas at 12 months post-operation. Epithelial coverage and stromal cell ingrowth have resulted in neo-corneal tissues similar to the natural, unoperated cornea. Arrowheads, stromal cells.

MATERIALS & METHODS

8-Arm PEG-Maleimide (Mn=41800) was purchased from Creative PEGWorks, NC, US. 8-Arm PEG-Thiol (Mn=10000) was purchased from JenKem Technology, Beijing, China. N-(3-dimethylaminopropyl)-N'-ethylcarbodiimide (EDC), N-hydroxysuccinimide (NHS).

General Procedure for Synthesis of CMP

All the CMP peptides given below (1-4), were synthesized on a Symphony automated peptide synthesizer (Protein Technologies Inc., Tucson, Ariz., U.S.A.) using standard fluorenylmethoxycarbonyl (Fmoc) chemistry. HCTU (ChemPep Inc., Wellington, Fla., USA) was used as the activating reagent. The 0.1 mmol scale synthesis used Fmoc-Gly-PEG-PS resin (Applied Biosystems, Life Technologies Europe BV, Sweden) and five-fold excess of amino acids in each coupling. The resultig peptides were cleaved from the resin by treatment with a mixture of trifluoroacetic acid (TFA), water and triisopropylsilane (TIS) (95:2.5:2.5 v/v; 10 mL per gram of polymer) for 2 h at ambient temperature. They were then filtered and the TFA was evaporated. The CMP 5 was then precipitated by the addition of cold diethyl ether, centrifuged and lyophilized. Purification was done using reversed-phase HPLC on a semi-preparative C-18 column (Grace Vydac, Helsingborg, Sweden) and peptide identity was confirmed by their MALDI-TOF spectra.

1. Cys-Gly-(Pro-Lys-Gly)$_4$(Pro-Hyp-Gly)$_4$(Asp-Hyp-Gly)$_4$ (SEQ ID NO 3) peptide identity was confirmed by their MALDI-TOF spectra (M+1, 3518).
2. Cys-Gly-(Pro-Lys-Gly)$_4$(Pro-Hyp-Gly)$_4$(Glu-Hyp-Gly)$_4$ (SEQ ID NO 4) peptide identity was confirmed by their MALDI-TOF spectra (M+1, 3574).
3. Cys-Gly-(Pro-Lys-Gly)$_4$(Pro-Hyp-Gly)$_4$(Asp-Hyp-Gly)$_4$-Gly-Gly-(Pro-Lys-Gly)$_4$(Pro-Hyp-Gly)$_4$(Asp-Hyp-Gly)$_4$ (SEQ ID 5) peptide identity was confirmed by their MALDI-TOF spectra (M+1, 6972).
4. Cys-Gly-Gly-Gly-Gly-(Pro-Lys-Gly)$_4$(Pro-Hyp-Gly)$_4$(Asp-Hyp-Gly)$_4$ (SEQ ID NO 6) peptide identity was confirmed by their MALDI-TOF spectra (M+1, 3689).
5. Cys-Gly-(Pro-Lys-Gly)$_4$(Pro-Hyp-Gly)$_4$(Asp-Hyp-Gly)$_4$-Arg-Gly-Asp-Ser-Pro-Gly (SEQ ID NO 7) peptide identity was confirmed by their MALDI-TOF spectra (M+1, 4088).
6. Cys-Gly-(Pro-Lys-Gly)$_4$(Pro-Hyp-Gly)$_4$(Asp-Hyp-Gly)$_4$-Ile-Lys-Val-Ala-Val-Gly (SEQ ID NO 8) peptide identity was confirmed by their MALDI-TOF spectra (M+1, 4086).

Synthesis of PEG-CMP

Solution of CMP in water and solution of 8-Arm PEG-Maleimide in DMSO was mixed at the molar ratio of PEG-Maleimide: CMP=1:3 or 1:5. After 4 days of continuous stirring at room temperature. the mixture was dialyzed through a dialysis membrane (12-14,000 molecular weight, Spectrum Laboratories, Inc., CA, US). After dialysis the solution was lyophilized to get solid PEG-CMP.

Molar composition of PEG:CMP is 1:8 in this example. Please note that this composition will change according to the number of functional arms present on the scaffold. In above example, since we have used 8-arm PEG, we can attach only 8 CMP peptide units to one PEG (template).

Characterisation of the Conjugate CMP with PEG

The bio-conjugation of CMP with 8-arm PEG Maleimide was characterized using $^1$H NMR, on an Oxford 300 MHz spectrometer (Varian, Calif., US) at room temperature. Briefly 1% solutions of PEG-maleimide and CMP-PEG were made in $C_2D_6OS$ (Dimethyl-$d_6$ sulfoxide, Armar Chemicals, Döttingen, Switzerland). The resonance of deuterated solvent ($C_2D_6OS$, $\delta$=2.5) was used as an internal standard.

The triple helical structure of CMP and CMP-PEG were evaluated using Chirascan™ CD Spectrometer (Applied Photophysics Ltd., Surrey, UK). Briefly, 1% of sample solutions were prepared and a quartz cell of 0.1 cm path length was used to record the CD spectra at 180-260 nm wavelengths, at a scan rate of 1 nm/s at room temperature.

Synthesis of Methacrylated PEG-CMP (MA-PEGCMP)

Freeze dried collagen was dissolved in Milli Q water and gently stirred. The pH of collagen solution was increased to pH 10 and methacrylic anhydride at a molar ratio of 5:1 (with respect to number of lysine amine groups in CMP) was added subsequently drop-wise at room temperature. The reaction mixture was dialyzed against distilled water (pH 10) using 12-14 kDa cutoff dialysis tubing (Spectrum Laboratories, Inc., CA, US) for 2-3 days to remove reaction by-products and lyophilized and stored at 4° C. until further use.

Fabrication of CMP Hydrogels/Implants using EDC Crosslinking

T-piece mixing system was used to make hydrogel with PEG-CMP, which was previously described [4]. For making the hydrogel 500 mg of 12% (w/w) PEG-CMP was taken into a 2 ml glass syringes. Calculated volumes of N-(3-dimethylaminopropyl)-N'-ethylcarbodiimide (EDC) (5% w/v) and N-hydroxysuccinimide (NHS) (10% w/v) in water were added. Molar equivalent ratio of PEG-CMP-NH$_2$: EDC was 1:0.4 (or 1:2) and EDC: NHS was 1:1. All addition followed by thorough mixing prior to moulding the hydrogel into flat sheets or cornea shape implants.

Fabrication of CMP Hydrogels using Photoinitiator

T-piece mixing system was used to make hydrogel with PEG-CMP, which was previously described [4]. 500 mg of 12% MA-PEGCMP was mixed with 2% (w.r.t MA-PEGCMP) Irgacure 2959 and mixed well. The solution from was then casted between two glass slide/mold with spacers of desired thickness and exposed to UV 365 nm wavelength for 10 to 15 min.

Fabrication of RHCIII and RHCIII-MPC Hydrogels/Implants

Two control hydrogels were made; one from 18% human recombinant collagen type III (Fibrogen) (RHC-III) and another one was from RHC-III with 2-methacryloyloxyethyl phosphorylcholine (MPC) (RHCIII-MPC). RHCIII-MPC was made by following previously published procedure [4]. 500 mg of 18% (w/v) RHC-III was buffered with 150 μl of 0.625 M MES buffer and mixed with calculated volume of MPC and PEGDA solution at 4° C. The Collagen:MPC ratio was 2:1 (w/w) and the MPC: PEGDA ratio was 3:1 (w/w). Calculated volume of APS (4% w/v) and TEMED (2% v/v) in MES were added in the Collagen-MPC-PEGDA solution. The ratio of MPC: APS was 1: 0.3 (w/w) and the ratio of APS: TEMED was 1:0.77 (w/w). Calculated volumes of EDC (5% w/v) and NHS (10% w/v) in MES were added. Molar equivalent ratio of Collagen-NH2: EDC was 1:0.4 and EDC: NHS was 1:1.

For RHC-III hydrogel, only NHS and EDC were added following above-mentioned procedure.

For all hydrogels, after adding EDC the final mixed solution was immediately dispensed onto a glass slide and pressed with another glass slides by keeping spacer of 500 μm or appropriate size as needed. The moulded solution was kept at 100% humidity. After demoulding, hydrogels were washed with sterilized phosphate buffered saline (PBS). For getting cornea shape construct, terminal mixed collagen/PEG-CMP solutions were casted into cornea shape moulds.

Our approach is 3-fold. 1) to use the base template (A) which is stable against enzymatic degradation and supports the cellular ingrowth promoting regeneration 2) modify homogeneously the central core with desired dimensions using synthetic polymer blocking the vessel ingrowth. 3) Surface modification of either the whole implant or central core with polymer/bioactive moieties for desired cellular response.

Characterisation of Hydrogels

All samples were tested in triplicate. After demoulding the hydrogels were kept in PBS for 24 hours. The wet weight of hydrogels ($W_0$) was obtained after gentle blotting on filer paper to remove surface water. The samples were then dried under vacuum until a constant weight (W) was obtained. The total equilibrated water content of the hydrogels (Wt) was calculated according to the following equation: Wt={(W−W0)/W)}×100%.

Optical properties such as transmission of white light and back-scattering were measured at room temperature using a custom-built instrument[2] The percent transmission of the samples was compared to the open beam intensity. The relative percent of light back scattered from the collimated beam by the sample was measured with a circular array of 8 photodiodes each at 30 degrees off axis.

The mechanical properties of CMP-PEG hydrogels were measured by using an Instron universal test machine (Biopuls 3343, High Wycombe, UK) equipped with Bluehell2 software. The measurements were carried out under water-immersion at 37° C. Dumb-bell shaped hydrogels of 500 μm thick with a gauge length of 14×6 mm and grips at each end of 10×6 mm, were cast in moulds. The mechanical testing was carried out using a 50 N load cell with a crosshead speed of 10 mm/min.

The resistance of CMP-PEG and RHC-MPC hydrogels to collagenase was determined as we previously described[3]. Hydrogels were placed in a vial containing 5 U/mL collagenase from *Clostridium histolyticum* (Sigma-Aldrich, St. Louis, USA in 0.1 M Tris-HCI (pH 7.4) and 5 mM CaCl$_2$ at 37° C. The collagenase solution was changed at every 8 hours and the percent residual mass of the sample was measured at different time points.

High Pressure Freezing Transmission Electron Microscopy (TEM)

CMP-PEG and RHC-MPC hydrogels were processed for TEM using a high pressure freezing technique. Approximately 1.5 mm×1.5 mm×150 μm of each hydrogels were dissected out to fit into a Leica high-pressure freezer membrane carrier. The samples were high pressure frozen using a Leica EMPACT2 high-pressure freezer (Leica Microsystems GmbH, Vienna, Austria). Vitrified specimens were then freeze substituted at −80° C. in 2% osmium/acetone, 1% tannic acid/acetone and 1% uranyl acetate/acetone for 88 h. Gels were then inserted in Araldite resin at 60° C. for 24 hrs. Sections of around 110 nm were cut and placed on 1 mm peloform-coated slot grids. Examination was carried out at 80 kV in a JEOL 1010 transmission electron microscope (JEOL, Tokyo, Japan).

Base Template

The base template is a bio- and immune compatible, biointeractive material that can be used as a scaffold for stimulating in-growth of host cells (stem or progenitor cells) to differentiate and re-form a healthy version of the original tissue. As such we have fabricated base templates based on ECM macromolecules that have been responsible for the original development of the cornea The base template will be one of the following.

1) CMP hydrogels
2) RHCIII/Porcine collagen crosslinked with EDC NHS
3) RHCIII+MPC hydrogels.

Central Polymer (Optical) Core

This is the "core" of the invention, the ability to convert a regular corneal implant into a prosthesis as indicated by the patient's condition. Essentially an acrylated monomer solution with UV initiator Irgacure 2959 is added at the center of hydrogel and allow it to diffuse in (over 15 min) hydrogels. The 15 min time interval allows for conversion of an implant from a regenerative implant to prosthesis during surgery. Gels were exposed to UV-A at 360 nm for 15 mins to form an optical core.

CMP-HEMA+PEGMEM Prosthesis

12% CMP hydrogels were made using EDC-NHS chemistry. Photoinitiator (Irgacure 2959) was dissolved in 1 mL of HEMA and heated up to 60° C. to dissolve the Photoinitiator in HEMA solution. Similarly 2 wt % of Photoinitiator (Irgacure 2959) solution in PEGMEM was also made. 10 μL of HEMA containing Photoinitiator along with 10 μL of PEGMEM (1:1 volume ratio) was dropped in the center of CMP hydrogels and allowed to diffuse inside the hydrogels for 15 mins (Final conc. Of PI—2 wt %).

After 15 mins, the sample was exposed to UV 365 nm for 15 mins. After exposing it to UV, the samples were stored in room temperature for 10 mins to give some curing time of polymers and immediately washed with distilled water to remove the unreacted reactants.

CMP—HEMA+MPC Prosthesis

12% CMP hydrogels were made using EDC-NHS chemistry. 2 wt % of Photoinitiator (Irgacure 2959) was dissolved in 1 mL of HEMA and heated up to 60° C. to dissolve the Photoinitiator in HEMA solution. Similarly 10 wt % of MPC solution was made in distilled water.

20 μL of HEMA containing Photoinitiator with 5 μL of MPC was dropped in the center of CMP hydrogels and allowed to diffuse inside the hydrogels for 15 mins (Final conc. of Photoinitiator—1.6 wt %). After 15 mins, the sample was exposed to UV 365 nm for 15 mins. After exposing it to UV, the samples were stored in room temperature for 10 mins to give some curing time of polymers and immediately washed with distilled water to remove the unreacted reactants.

Subcutaneous Implantation in Rats

After approval from the local ethical committee (Linköpings Djurförsöksetiska Nämnd) and in compliance with the Swedish Animal Welfare Ordinance and the Animal Welfare Act, CLP-PEG hydrogel samples, 1 cm diameter× 500 um thick, were implanted subcutaneously into rats as per ISO 10993-6 to test for local reaction to CMP-PEG hydrogels. Each sample was inserted into a subcutaneous pocket created by blunt dissection in the paravertebral region of the back of a 9 week old Wistar rats. A total of 4 samples were evaluated in a total of 4 rats. Implantation sites were checked for healing, skin appearance, and re-growth of hair post-surgery. After 90 days, the rats were euthanized and the implants were harvested and fixed in 4% paraformaldehyde for histopathological examination following haematoxylin and eosin staining (H&E).

CLP-PEG Implantation and Evaluation in Mini-Pig Corneas

In preparation for clinical translation, in compliance with the OECD Principle of Good Laboratory Practice (GLP), ENV/MC/CHEM (98) 17, 1997, and with local ethical permission, one CLP-PEG implant was grafted into one cornea each of four Gottingen mini-pigs (Ellegaard, Denmark) by deep anterior lamellar keratoplasty (DALK), at Adlego Biomedical AB (Solna, Sweden). Animals were intubated and anaesthetized prior to surgery. The right cornea of each pig cornea was cut with a 6.5 mm circular trephine to a depth of 500 μm, and the corneal button was then manually dissected with a diamond knife and removed. Hydrogel implants were cut with 6.75 mm diameter trephine and placed into the wound bed. A piece of clinical human amniotic membrane (HAM) (St:Erik's Eye Hospital, Stockholm) was placed over the implant to suppress undesired inflammation and the implants were kept in place with overlying sutures. Upon completion of the surgery, an antibacterial and anti-inflammatory ophthalmic suspension (Tobraone with 3 mg/ml dexamethasone and 1 mg/mL tobramycine, Alcon, Sweden) was administered. The maintenance dose was 1 drop, 3 times daily for 5 weeks. The unoperated contralateral corneas and RHC-MPC hydrogels served as controls.

The health status of all animals were monitored throughout the 12 month study. The corneas and implants were evaluated before surgery, at 5 weeks and then at 3, 6, 9 and 12 months after surgery. The examinations were performed by a surgeon who was blinded to which animals received CMP-PEG or RHC-MPC hydrogels. These examinations consisted of slit lamp biomicroscopy (to evaluate haze from a 0 to +4 scale, any neovascularization and general health of the eye), pachymetry to measure cornea/implant thickness, Schrimer's tear test to evaluate the extent of the tear film (tear strips from TearFlo, Hub Pharmaceuticals, Rancho Cucamonga, Calif., USA), intraocular pressure (using a TonoVet tonometer, Icare Finland Oy, Vantaa, Finland), esthesiometry to determine corneal sensitivity as measure of nerve function (using a Cochet-Bonnet esthesiometer; Handaya Co., Tokyo, Japan) and in vivo confocal microscopy (Heidelberg HRT3 with a Rostock Cornea Module, Heidelberg Engineering GmbH, Dossenheim, Germany) to access in-growth of corneal cells, nerves and any blood vessels or inflammatory cells.

Evaluation of Regeneration

At 12 months post-operative, animals were euthanized after their final clinical eye examination. The entire implanted cornea and unoperated contralateral controls were dissected out with 2-3 mm of the surrounding sclera. A central 3 mm diameter, full-thickness sample was trephined out and snap frozen for collagen analyses. The remaining cornea was divided into pieces, with half fixed in 4% buffered paraformaldehyde and processed for histopathological examination by a $3^{rd}$ party certified veterinary pathologist (BioVet AB, Sollentuna, Sweden).

For protein analyses, each frozen 3 mm diameter sample from operated and control corneas was weighed and resuspended in 10 mM HCl containing 1 mg/mL pepsin. The samples were digested with porcine pepsin at 2-8° C. for 96 h and the soluble fraction (supernatant) was recovered by centrifugation. An aliquot of the supernatant was mixed with NuPAGE 4X LDS sample buffer (Life Technologies) denatured at 75° C. for 8 minutes and analyzed on 3-8% Tris-acetate gels under non-reducing conditions. Proteins were visualized by staining with Gelcode Blue. Stained gels were scanned and band intensity was quantitated using a GE Healthcare ImageQuant350 equipped with ImageQuant TL image analysis software version 7.0.

To determine if the initial CMP-PEG implant had been completely remodelled or was still present within the regenerated neo-corneas, FTIR spectra of CMP and PEG-maleimide alone, and non-implanted CMP-PEG hydrogel was compared to cornea samples from CMP-PEG implanted eyes and control eyes. The samples were scanned between 4000 to 400 $cm^{-1}$ using VERTEX 70 FTIR spectrometer (Bruker, Billerica, Mass., USA) at the resolution of 4 $cm^{-1}$ averaging 200 scans.

EXAMPLE 1

After CMP synthesis CMP is mixed with the same or different templating monomers such as for example PEG-Maleimide to assist the assembly of triple helical polypeptides (FIGS. 1 and 2). CMP can be further functionalised with different biomolecules or markers (FIG. 3). The hydrogels comprising the CMP peptide are self-supporting and robust to retain shape (FIG. 4). Hydrogels can be modified by adding one or more additional polymers forming a core (FIG. 6). Table 1 compares the properties of CMP-PEG corneal implants with human corneas.

EXAMPLE 2

Hydrogels comprising the CMP are stable in the presence of collagenase. As shown in FIG. 5A) the residual weight of the CMP comprising hydrogel is reduced by approximately 10% in the presence of collagenase whereas hydrogels comprising collagen or recombinant human collagen (3H, 3H-MPC, Fibrinogen, Fibrinogen-MPC, Theracol, Theracol-IKVAV or Theracol-YIGSR) show significant digestion after 22 h or 50 h respectively. CMP comprising hydrogels are highly biocompatible and support cell adhesion and growth. FIG. 5B shows coverage by corneal epithelial cells in vitro. The ability to support cell adhesion and growth is retained even after exposure to enzyme.

CMP-PEG hydrogels when examined under high pressure freezing transmission electron microscopy, showed fibril-like structures (FIG. 14A) similar to their RHC counterparts comprising full-length collagen fibrils (FIG. 14B).

EXAMPLE 3

Cell growth on the core material such as MPC-MMA one week after seeding is poor preventing cell and vessel ingrowth and allowing unhindered light transmission. Hydrogels comprising collagen-MPC and grown for one week show cell overgrowth similar to cells cultured for one week in tissue culture plates (FIG. 7).

CLP-PEG hydrogels supported growth of human corneal epithelial cells in culture without any cytotoxic effects, showing in vitro biocompatibility (data not shown). Subsequent subcutaneous implantation of the hydrogels into rats for 90 days confirmed biocompatibility (FIG. 14F) and hydrogel stability in vivo.

EXAMPLE 4

The CMP-comprising hydrogels can be easily patterned such as a for example a biotin-terminated pattern using photolithography or imprinting (FIG. 8). The patterned surfaces enable cell growth and/or adhesion. FIG. 9 shows fluorescence microscopy of images obtained from the surface of RHCIII-MPC hydrogels patterned with 30 µm (FIG. 9A) and 200 µm stripes (FIG. 9C) visualized by staining with an anti-fibronectin antibody [in red]. The corresponding images show corneal epithelial cells growing along the fibronectin stripes. These cells were exposed to a live-dead stain and are mainly green with only 1-2 red cells, showing that majority of cells are viable on the patterned stripes (FIG. 9B and FIG. 9D).

EXAMPLE 5

The comparison of pig corneas comprising RHCIII-MPC versus CLP-PEG at 12 months post-operation shows a similar epithelial overgrowth and in-growth of nerves and stromal cells (FIG. 11). Both regenerated corneas showed comparable features to the control, unoperated healthy cornea also shown in the amounts of collagen recovered from the regenerated neo-corneas after RHCIII-MPC and CLP-PEG implantation versus control, unoperated healthy corneas (FIGS. 11 and 12).

Figure 16:
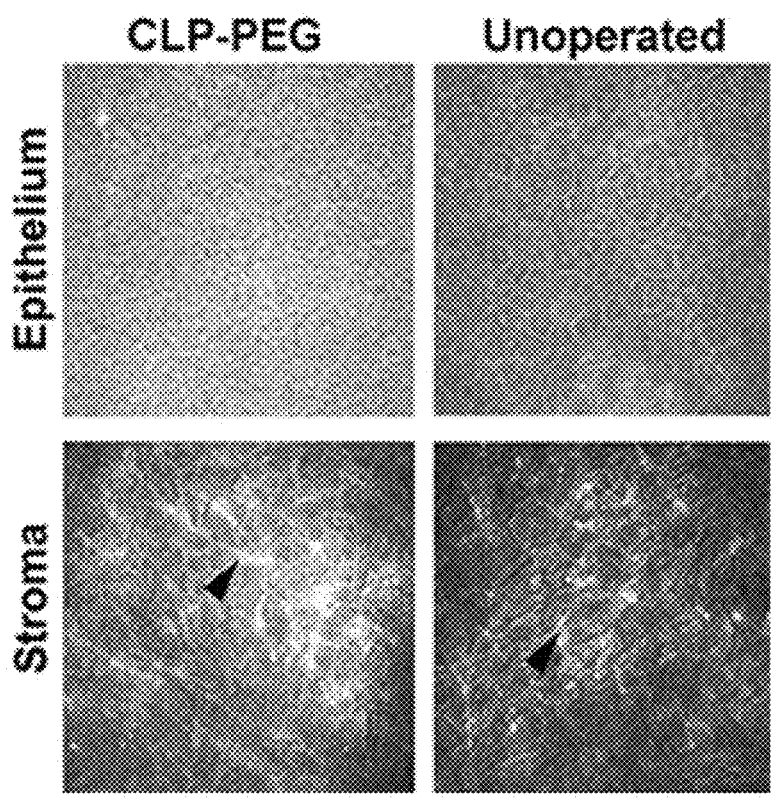

Histologically, regenerated neo-corneas (FIG. 15A) resembled unoperated controls (FIG. 15B). In vivo confocal microscopy, which allows real-time imaging of the pigs' eyes showed that the corneal epithelial and stromal cells had grown into the initially acellular hydrogels (FIG. 16). Corneal nerves had also grown into the implants (FIG. 15C) resulting in neo-corneas that resembled their unoperated contralateral counterparts (FIG. 15D). These nerves were functional as shown by their touch sensitivity and contribution to tear film restoration (Table 1). Surprisingly, FTIR spectroscopy revealed CMP and PEG profiles, suggesting that the original implant could be present at 12 months post-operation despite the deposition of cornea collagen by incoming cells (FIG. 15E). A synthetic scaffold that remains while allowing for full regeneration of corneal tissue and nerves would allow the implant to be used either as a regenerative implant or as a prosthetic device that would allow some stromal and epithelial cell in-growth for integration within the host.

EXAMPLE 6

SDS-PAGE profiles of pepsin soluble proteins extracted from the implant region of operated corneas (O), after separation on a 3-8% gradient Tris-acetate gel. Controls comprise identically processed proteins from the unoperated control cornea (C), porcine collagen type 1, pepsin standard, pepsin digest from rat cornea (+) pepsin digest from an unused rhCIII implant (−). This shows that both RHCIII-MPC implanted eyes (animals 1-4) and CLP-PEG implanted eyes (animals 5-8) were remodelled to show type I and type V collagen instead of the initial type III collagen (FIG. 13).

TABLE 1

Properties of CMP-PEG corneal implants in comparison to human corneas

| Properties | Transmission (%) | Backscatter (%) | Tensile Strength (MPa) | Elongation (%) | Modulus (MPa) | Water content (%) |
|---|---|---|---|---|---|---|
| PEG-CMP | 92.4 ± 0.95 | 0.90 ± 0.17 | 0.07 ± 0.02 | 58.30 ± 4.49 | 0.18 ± 0.06 | 91.65 ± 1.10 |
| Human Cornea* | 87.1 ± 2.0 | <3 | 3.81 ± 0.40 | — | 3-13 | 78 |

*Buznyk, O. et al. *Clin. Transl. Sci.* (2015).

References

1. Mirazul Islam, M. et al. *Acta. Biomater.* 12, 70-80 (2015).
2. Priest, D & Munger R. *Invest. Ophthalmol. Vis. Sci.* 39, S352 (1998).
3. Deng, C. et al. *Acta Biomater.* 6, 187-194 (2012).
4. Liu Y. et.al Invest Ophthalmol Vis Sci. 2006 May;47(5):1869-75.

The invention claimed is:

1. A peptide comprising an amino acid sequence wherein said peptide comprises at least four amino acid motifs represented in the following formula:

(Xaa$_1$ Xaa$_2$)$_w$(Xaa$_3$-Xaa$_4$-Xaa$_5$)$_x$(Xaa$_6$-Xaa$_7$-Xaa$_8$)$_y$ (Xaa$_9$-Xaa$_{10}$-Xaa$_{11}$)$_z$ (Xaa$_1$ Xaa$_2$)$_w$ is a first amino acid motif wherein Xaa$_1$ is a thiol containing amino acid and Xaa$_2$ is a glycine amino acid wherein w equals 1 or more, (Xaa$_3$-Xaa$_4$-Xaa$_5$)$_x$ is a second amino acid motif wherein Xaa$_3$ is proline, Xaa$_4$ is lysine, Xaa$_5$ is glycine wherein x equals 1-4, (Xaa$_6$-Xaa$_7$-Xaa$_8$)$_y$ is a third amino acid motif wherein Xaa$_6$ is proline, Xaa$_7$ is hydroxyproline, Xaa$_8$ is glycine wherein y equals 1-4; and (Xaa$_9$-Xaa$_{10}$-Xaa$_{11}$) is a fourth amino acid motif wherein Xaa$_9$ is aspartic acid or glutamic acid, Xaa$_{10}$ is hydroxyproline, Xaa$_{11}$ is glycine wherein z equals 1-4.

2. The peptide according to claim 1, wherein said thiol containing amino acid is cysteine.

3. The peptide according to claim 1 wherein w is 2 or more; wherein said peptide comprises at least 1, 2, 3 or 4 repeats of said first amino acid motif.

4. The peptide according to claim 1, wherein said peptide comprises at least, 1, 2, 3 or 4 repeats of said second amino acid motif.

5. The peptide according to claim 1 wherein said peptide comprises at least 1, 2, 3 or 4 repeats of said third amino acid motif.

6. The peptide according to claim 1 wherein said peptide comprises at least 1, 2, 3 or 4 repeats of said fourth amino acid motif.

7. The peptide according to claim 1 wherein said peptide comprises the amino acid sequence selected from the group consisting of:

Xaa$_1$ -Gly-(Pro-Lys-Gly)$_4$(Pro-Hyp-Gly)$_4$(Asp-Hyp-Gly)$_4$ (SEQ ID NO: 2)

wherein Xaa$_1$ is a natural or modified thiol containing amino acid Cys-Gly-(Pro-Lys-Gly)$_4$(Pro-Hyp-Gly)$_4$ (Asp-Hyp-Gly)$_4$ (SEQ ID NO: 3), or Cys-Gly-(Pro-Lys-Gly)$_4$(Pro-Hyp-Gly)4(Glu-Hyp-Gly)$_4$ (SEQ ID NO: 4)

Cys-Gly-(Pro-Lys-Gly)$_4$(Pro-Hyp-Gly)$_4$(Asp-Hyp-Gly)$_4$-Gly-Gly-(Pro-Lys-Gly)$_4$(Pro-Hyp-Gly)$_4$(Asp-Hyp-Gly)$_4$; (SEQ ID NO: 5) Cys-Gly-Gly-Gly-Gly-(Pro-Lys-Gly)$_4$(Pro-Hyp-Gly)$_4$(Asp-Hyp-Gly)$_4$(SEQ ID NO: 6); Cys-Gly-(Pro-Lys-Gly)$_4$(Pro-Hyp-Gly)$_4$(Asp-Hyp-Gly)$_4$ -Arg-Gly-Asp-Ser-Pro-Gly (SEQ ID NO: 7);

Cys-Gly-(Pro-Lys-Gly)$_4$(Pro-Hyp-Gly)$_4$(Asp-Hyp-Gly)$_4$ -Ie-Lys-Val-Ala-Val-Gly (SEQ ID NO: 8);

wherein said peptide is a collagen mimetic peptide.

8. The peptide according to claim 1 wherein said peptide is at least 11 amino acids in length; wherein said peptide comprises 11 to 38 amino acids.

9. The peptide according to claim 1 wherein said peptide is derivatized by chemical modification to provide one or more reactive groups.

10. The peptide according to claim 9 wherein said peptide is modified by addition of one or more functional groups selected from the group consisting of: thiol, methyacrylate or acrylate functional groups.

11. The peptide according to claim 9 wherein said modified peptide comprises polyethylene glycol; polyethylene glycol-maleimide or polyethylene glycol diacrylate or polyethylene glycol methacrylate.

12. The peptide according to claim 11 wherein said polyethylene glycol-maleimide is at least 2, 4, 6 or 8 arm polyethylene glycol-maleimide, or more than 8 arm polyethylene glycol-maleimide.

13. A hydrogel comprising: a plurality of modified collagen mimetic peptides according to claim 1, chemically cross linked into a network.

14. The hydrogel according to claim 13 wherein said hydrogel comprises one or more natural or synthetic biopolymers chemically cross linked to said network.

15. A corneal implant comprising a hydrogel according to claim 13.

16. The corneal implant according to claim 15 wherein said corneal implant comprises a matrix part comprising a hydrogel and a core part wherein the core part is substantially centrally located in the matrix part and comprises polymerized olefinic or UV polymerizable monomers, or a mixture thereof, the hydrogel of the matrix material and one or more antifouling polymers/agents characterised in that the core part is substantially transparent and free of cells/vessels when in use.

17. The corneal implant according to claim 16 wherein the surface of the matrix material and/or the core material is modified and/or patterned with N-hydroxysulfosuccinimide (NHS), polypeptides such as YIGSR (SEQ ID NO: 9), IKVAV (SEQ ID NO: 10), RGD, ECM proteins, fibronectin derived peptides, combinations of synergestic peptides, DGEA peptide from collagen, antibodies, glycosaminoglycans, motifs from growth factors, or pharmaceutically active substances.

18. A surgical method for the repair or replacement of diseased or damaged corneal tissue in a subject in need of corneal repair or damage comprising:
   i) providing a corneal implant according to claim 15;
   ii) attaching the corneal implant to the eye of said subject; and optionally
   iii) providing a protective covering to the repaired eye to facilitate healing.

19. The surgical method according to claim 18 wherein said disease is selected from the group consisting of: Fuchs' Dystrophy, iridocorneal endothelial syndrome, keratoconus, lattice dystrophy, ocular herpes infections and trachoma.

20. The corneal implant according to claim 18 wherein said damage is chemical damage or physical injury.

* * * * *

SEQUENCE LISTING

<160> NUMBER OF SEQ ID NOS: 10

<210> SEQ ID NO 1
<211> LENGTH: 11
<212> TYPE: PRT
<213> ORGANISM: Artificial Sequence
<220> FEATURE:
<223> OTHER INFORMATION: Collagen Mimetic Peptide
<220> FEATURE:
<221> NAME/KEY: misc_feature
<222> LOCATION: (1)..(1)
<223> OTHER INFORMATION: wherein X is any thiol containing amino acid
<220> FEATURE:
<221> NAME/KEY: misc_feature
<222> LOCATION: (1)..(2)
<223> OTHER INFORMATION: wherein the amino acid motif X Gly is repeated at least one time
<220> FEATURE:
<221> NAME/KEY: misc_feature
<222> LOCATION: (3)..(5)
<223> OTHER INFORMATION: wherein the amino acid motif Pro Lys Gly can be repeated between 1 to 4 times
<220> FEATURE:
<221> NAME/KEY: misc_feature
<222> LOCATION: (6)..(8)
<223> OTHER INFORMATION: wherein the amino acid motif PXG can be repeated between 1 to 4 times
<220> FEATURE:
<221> NAME/KEY: misc_feature
<222> LOCATION: (7)..(7)
<223> OTHER INFORMATION: wherein the amino acid X is hydroxyproline
<220> FEATURE:
<221> NAME/KEY: misc_feature
<222> LOCATION: (9)..(9)
<223> OTHER INFORMATION: wherein X is Asp or Glu
<220> FEATURE:
<221> NAME/KEY: misc_feature
<222> LOCATION: (9)..(11)
<223> OTHER INFORMATION: wherein the amino acid motif X X Gly can be repeated between 1 to 4 times
<220> FEATURE:
<221> NAME/KEY: misc_feature
<222> LOCATION: (10)..(10)
<223> OTHER INFORMATION: wherein the amino acid X is hydroxyproline

<400> SEQUENCE: 1

Xaa Gly Pro Lys Gly Pro Xaa Gly Xaa Xaa Gly
1               5                   10

```
<210> SEQ ID NO 2
<211> LENGTH: 38
<212> TYPE: PRT
<213> ORGANISM: Artificial Sequence
<220> FEATURE:
<223> OTHER INFORMATION: Collagen Mimetic Peptide
<220> FEATURE:
<221> NAME/KEY: misc_feature
<222> LOCATION: (1)..(1)
<223> OTHER INFORMATION: wherein X is any thiol containing amino acid
<220> FEATURE:
<221> NAME/KEY: misc_feature
<222> LOCATION: (2)..(38)
<223> OTHER INFORMATION: wherein X is hydroxyproline

<400> SEQUENCE: 2

Xaa Gly Pro Lys Gly Pro Lys Gly Pro Lys Gly Pro Lys Gly Pro Xaa
 1               5                  10                  15

Gly Pro Xaa Gly Pro Xaa Gly Pro Xaa Gly Asp Xaa Gly Asp Xaa Gly
             20                  25                  30

Asp Xaa Gly Asp Xaa Gly
         35

<210> SEQ ID NO 3
<211> LENGTH: 38
<212> TYPE: PRT
<213> ORGANISM: Artificial Sequence
<220> FEATURE:
<223> OTHER INFORMATION: Collagen Mimetic Peptide
<220> FEATURE:
<221> NAME/KEY: misc_feature
<222> LOCATION: (1)..(38)
<223> OTHER INFORMATION: wherein X is hydroxyproline

<400> SEQUENCE: 3

Cys Gly Pro Lys Gly Pro Lys Gly Pro Lys Gly Pro Lys Gly Pro Xaa
 1               5                  10                  15

Gly Pro Xaa Gly Pro Xaa Gly Pro Xaa Gly Asp Xaa Gly Asp Xaa Gly
             20                  25                  30

Asp Xaa Gly Asp Xaa Gly
         35

<210> SEQ ID NO 4
<211> LENGTH: 38
<212> TYPE: PRT
<213> ORGANISM: Artificial Sequence
<220> FEATURE:
<223> OTHER INFORMATION: Collagen Mimetic Peptide
<220> FEATURE:
<221> NAME/KEY: misc_feature
<222> LOCATION: (1)..(38)
<223> OTHER INFORMATION: wherein X is hydroxyproline

<400> SEQUENCE: 4

Cys Gly Pro Lys Gly Pro Lys Gly Pro Lys Gly Pro Lys Gly Pro Xaa
 1               5                  10                  15

Gly Pro Xaa Gly Pro Xaa Gly Pro Xaa Gly Glu Xaa Gly Glu Xaa Gly
             20                  25                  30

Glu Xaa Gly Glu Xaa Gly
         35

<210> SEQ ID NO 5
<211> LENGTH: 76
<212> TYPE: PRT
<213> ORGANISM: Artificial Sequence
<220> FEATURE:
<223> OTHER INFORMATION: Collagen Mimetic Peptide
```

<220> FEATURE:
<221> NAME/KEY: misc_feature
<222> LOCATION: (1)..(76)
<223> OTHER INFORMATION: wherin X is hydroxyproline

<400> SEQUENCE: 5

Cys Gly Pro Lys Gly Pro Lys Gly Pro Lys Gly Pro Lys Gly Pro Xaa
1               5                   10                  15

Gly Pro Xaa Gly Pro Xaa Gly Pro Xaa Gly Asp Xaa Gly Asp Xaa Gly
            20                  25                  30

Asp Xaa Gly Asp Xaa Gly Gly Pro Lys Gly Pro Lys Gly Pro Lys
        35                  40                  45

Gly Pro Lys Gly Pro Xaa Gly Pro Xaa Gly Pro Xaa Gly Pro Xaa Gly
    50                  55                  60

Asp Xaa Gly Asp Xaa Gly Asp Xaa Gly Asp Xaa Gly
65                  70                  75

<210> SEQ ID NO 6
<211> LENGTH: 41
<212> TYPE: PRT
<213> ORGANISM: Artificial Sequence
<220> FEATURE:
<223> OTHER INFORMATION: Collagen Mimetic Peptide
<220> FEATURE:
<221> NAME/KEY: misc_feature
<222> LOCATION: (1)..(41)
<223> OTHER INFORMATION: wherein X is hydroxyproline

<400> SEQUENCE: 6

Cys Gly Gly Gly Gly Pro Lys Gly Pro Lys Gly Pro Lys Gly Pro Lys
1               5                   10                  15

Gly Pro Xaa Gly Pro Xaa Gly Pro Xaa Gly Pro Xaa Gly Asp Xaa Gly
            20                  25                  30

Asp Xaa Gly Asp Xaa Gly Asp Xaa Gly
        35                  40

<210> SEQ ID NO 7
<211> LENGTH: 44
<212> TYPE: PRT
<213> ORGANISM: Artificial Sequence
<220> FEATURE:
<223> OTHER INFORMATION: Collagen Mimetic Peptide
<220> FEATURE:
<221> NAME/KEY: misc_feature
<222> LOCATION: (1)..(44)
<223> OTHER INFORMATION: wherein X is hydroxyproline

<400> SEQUENCE: 7

Cys Gly Pro Lys Gly Pro Lys Gly Pro Lys Gly Pro Lys Gly Pro Xaa
1               5                   10                  15

Gly Pro Xaa Gly Pro Xaa Gly Pro Xaa Gly Asp Xaa Gly Asp Xaa Gly
            20                  25                  30

Asp Xaa Gly Asp Xaa Gly Arg Gly Asp Ser Pro Gly
        35                  40

<210> SEQ ID NO 8
<211> LENGTH: 44
<212> TYPE: PRT
<213> ORGANISM: Artificial Sequence
<220> FEATURE:
<223> OTHER INFORMATION: Collagen Mimetic Peptide
<220> FEATURE:
<221> NAME/KEY: misc_feature
<222> LOCATION: (1)..(44)
<223> OTHER INFORMATION: wherein X hydroxyproline

```
<400> SEQUENCE: 8

Cys Gly Pro Lys Gly Pro Lys Gly Pro Lys Gly Pro Lys Gly Pro Xaa
1               5                   10                  15

Gly Pro Xaa Gly Pro Xaa Gly Pro Xaa Gly Asp Xaa Gly Asp Xaa Gly
            20                  25                  30

Asp Xaa Gly Asp Xaa Gly Ile Lys Val Ala Val Gly
        35                  40

<210> SEQ ID NO 9
<211> LENGTH: 5
<212> TYPE: PRT
<213> ORGANISM: Artificial Sequence
<220> FEATURE:
<223> OTHER INFORMATION: laminin derived peptide

<400> SEQUENCE: 9

Tyr Ile Gly Ser Arg
1               5

<210> SEQ ID NO 10
<211> LENGTH: 5
<212> TYPE: PRT
<213> ORGANISM: Artificial Sequence
<220> FEATURE:
<223> OTHER INFORMATION: laminin derived peptide

<400> SEQUENCE: 10

Ile Lys Val Ala Val
1               5
```